United States Patent
Guevremont et al.

(10) Patent No.: US 7,274,014 B2
(45) Date of Patent: Sep. 25, 2007

(54) APPARATUS AND METHOD FOR ADJUSTMENT OF ION SEPARATION RESOLUTION IN FAIMS

(75) Inventors: Roger Guevremont, Ottawa (CA); by Maria Guevremont, legal representative, Ottawa (CA); James T. Kapron, Ottawa (CA)

(73) Assignee: Thermo Finnigan LLC, San Jose, CA (US)

( * ) Notice: Subject to any disclaimer, the term of this patent is extended or adjusted under 35 U.S.C. 154(b) by 40 days.

(21) Appl. No.: 11/285,148

(22) Filed: Nov. 23, 2005

(65) Prior Publication Data

US 2006/0237643 A1    Oct. 26, 2006

Related U.S. Application Data

(60) Provisional application No. 60/630,193, filed on Nov. 24, 2004.

(51) Int. Cl.
*H01J 49/40* (2006.01)
(52) U.S. Cl. ...................... 250/287; 250/286
(58) Field of Classification Search ................ 250/287, 250/286, 281, 282
See application file for complete search history.

(56) References Cited

U.S. PATENT DOCUMENTS

| | | | |
|---|---|---|---|
| 6,653,627 B2 | 11/2003 | Guevremont et al. | |
| 6,727,496 B2 | 4/2004 | Miller et al. | |
| 6,770,875 B1 | 8/2004 | Guevremont et al. | |
| 2004/0124350 A1 | 7/2004 | Miller et al. | |
| 2006/0151694 A1* | 7/2006 | Guevremont et al. | 250/292 |

OTHER PUBLICATIONS

Guevremont et al. "Atmospheric Pressure Ion Focusing in a High-Field Asymmetric Waveform Ion Mobility Spectrometer", Review of Scientific Instruments, 1999, vol. 70, No. 2, pp. 1370-1383.

* cited by examiner

*Primary Examiner*—Kiet T. Nguyen
(74) *Attorney, Agent, or Firm*—Freedman & Associates

(57) ABSTRACT

An apparatus for controllably varying specificity of a FAIMS-based ion separation includes a FAIMS analyzer region defined between a first electrode surface and a second other electrode surface. The FAIMS analyzer region is in communication with an ionization source for providing a flow of ions including a known ion, and with an ion outlet for extracting ions including the known ion from the FAIMS analyzer region. The first and second electrode surfaces are for having an asymmetric waveform voltage applied thereacross for defining an average ion flow path for the known ion traversing therebetween. An actuator is provided for controllably moving the first electrode surface relative to the second electrode surface for controllably varying the length of the average ion flow path.

24 Claims, 19 Drawing Sheets

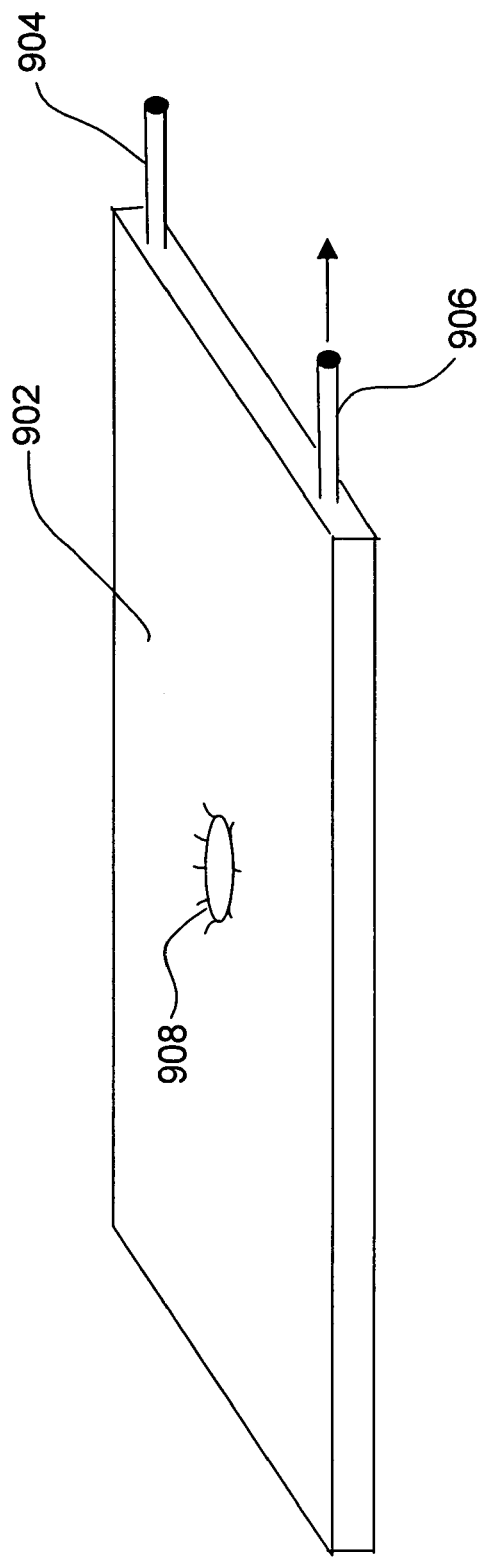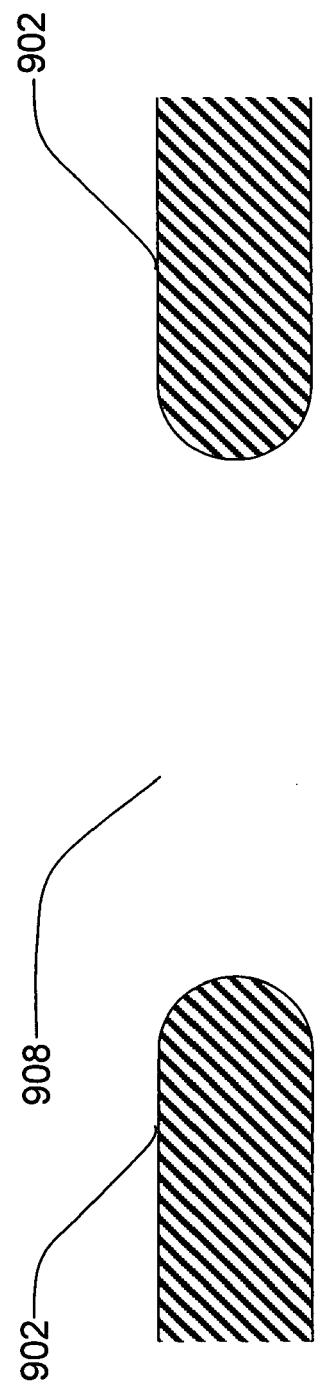
Figure 9a
Figure 9b

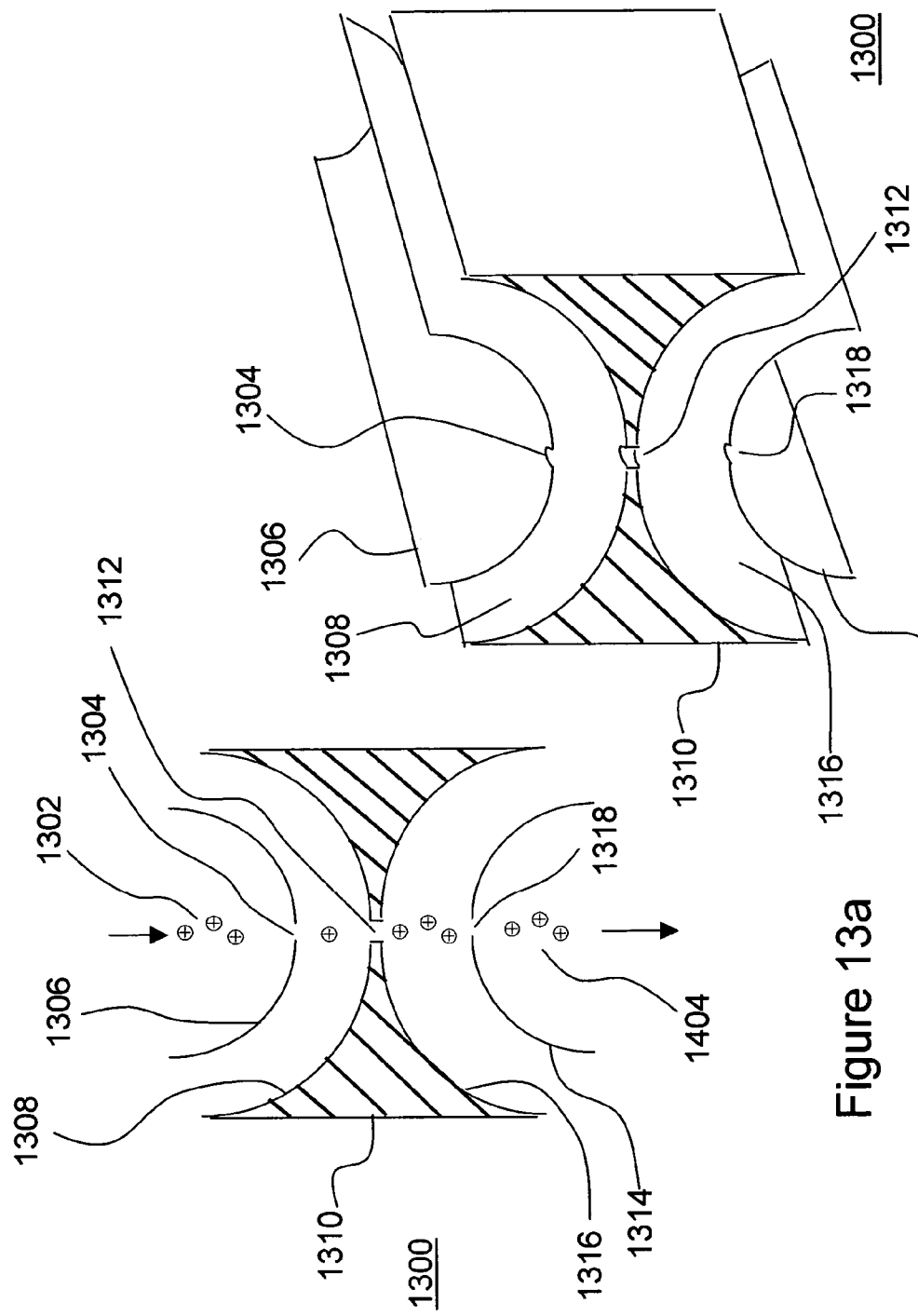

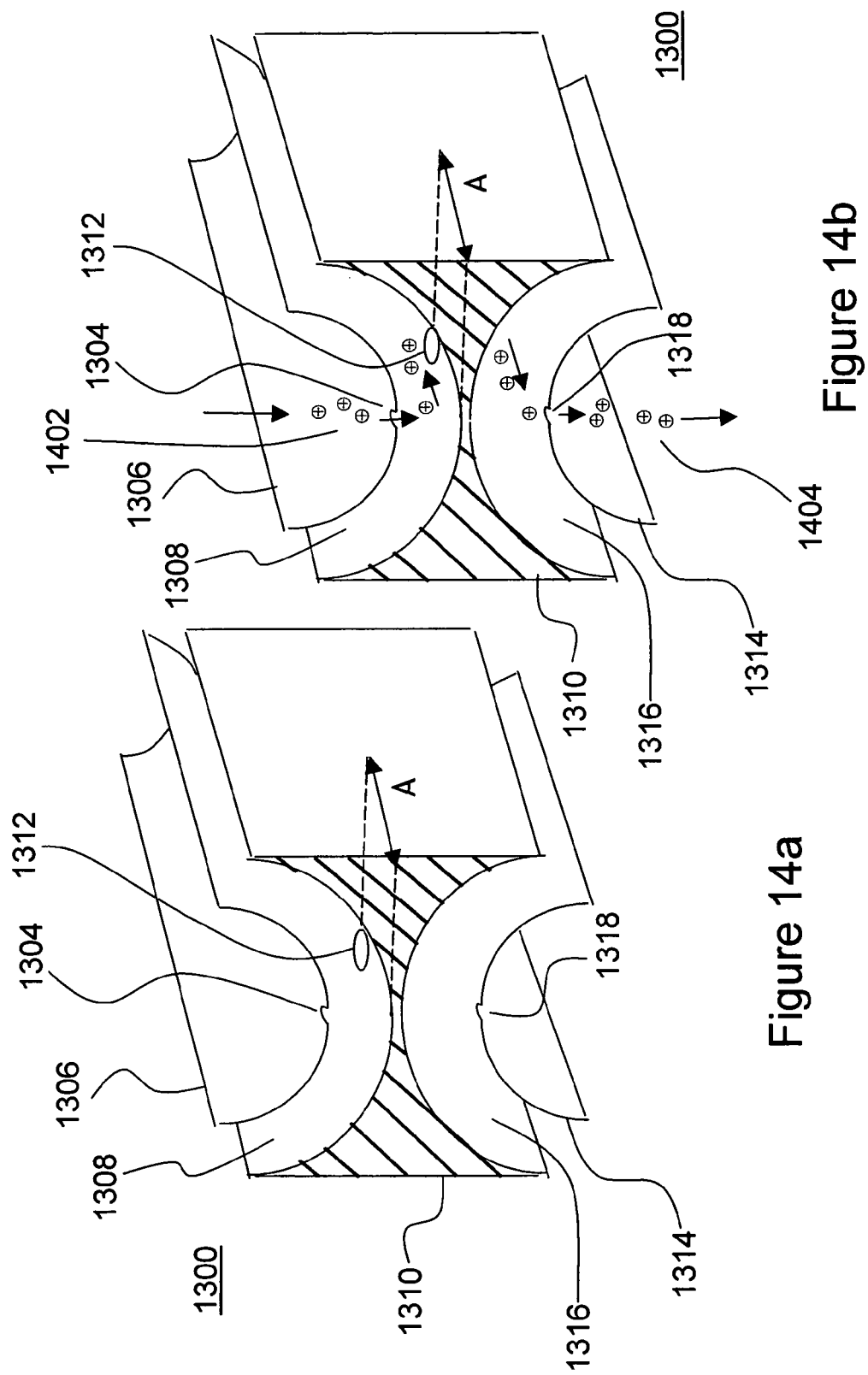

APPARATUS AND METHOD FOR ADJUSTMENT OF ION SEPARATION RESOLUTION IN FAIMS

This application claims benefit from U.S. Provisional application 60/630,193 filed Nov. 24, 2004, the entire contents of which are incorporated herein by reference.

FIELD OF THE INVENTION

The instant invention relates generally to High Field Asymmetric Waveform Ion Mobility Spectrometry (FAIMS), and more particularly to an apparatus and method for controllably varying specificity of a FAIMS-based ion separation.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in FAIMS on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform, an ion moves with a y-axis velocity component given by $V_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis during the negative cycle of the waveform. If at $E_H$ the mobility $K_H > K$, the ion experiences a net displacement from its original position relative to the y-axis. For example, if a positive ion travels farther during the positive portion of the waveform, for instance $d_H > d_L$, then the ion migrates away from the second electrode and eventually is neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

In an analytical instrument that includes (1) a condensed phase separation including for example one of liquid chromatography (LC) or capillary electrophoresis, (2) an atmospheric pressure ionization source including for example electrospray ionization (ESI) or atmospheric pressure photoionization (APPI), (3) an atmospheric pressure gas phase ion separator including for example high-field asymmetric waveform ion mobility spectrometer (FAIMS) and (4) a detection system including for example mass spectrometry (MS), it is advantageous to support switching to convert the function of the intermediate gas phase separation device (FAIMS for example) from a mode of separation to a mode in which the ions are not separated. This non-separating mode is called "total ion transmission mode" (TITM). The TITM is beneficial for reviewing the mixture of ions that are arriving at the intermediate separation device, in order to assess whether any ions are being overlooked by application of the intermediate separation stage. The TITM mode in FAIMS is analogous to the rf-only mode of a quadrupole mass spectrometer, in which mode of operation a wide range of ions is transmitted simultaneously through the quadrupole. This rf-only mode supports tandem arrangement of several quadrupole devices, with one or more of the quadrupole devices operated optionally in non-separation mode so that the separation of ions only occurs in one of the series of tandem quadrupole devices.

SUMMARY OF THE INVENTION

It is an object of at least some embodiments of the instant invention to provide a FAIMS device that is selectively operable in a first separation mode and in a second separation mode, the second separation mode having an ion separation resolution that differs from the first separation mode.

It is a further object of at least some of the embodiments of the instant invention to provide a FAIMS device that is selectively operable in a conventional FAIMS separating mode and in a total ion transmission mode (TITM).

According to an aspect of the instant invention, there is provided an apparatus for controllably varying specificity of a FAIMS-based ion separation, comprising: a first electrode comprising a first electrode surface; a second electrode comprising a second electrode surface, the second electrode spaced-apart from the first electrode along a first direction such that the second electrode surface faces the first electrode surface and overlaps therewith along a second direction that is normal to the first direction so as to define a FAIMS analyzer region therebetween, the FAIMS analyzer region having an ion inlet end and an ion outlet end, the first electrode and the second electrode movable one relative to the other along the second direction for varying a length of the FAIMS analyzer region between the ion inlet end and the ion outlet end; and, an actuator for controllably relatively moving the first electrode along the second direction relative to the second electrode, for varying the length of the FAIMS analyzer region between the ion inlet end and the ion outlet end.

According to an aspect of the instant invention, there is provided an apparatus for controllably varying specificity of a FAIMS-based ion separation, comprising: a first generally cylindrical inner electrode having a first length; a second generally cylindrical inner electrode having a second length, the second generally cylindrical inner electrode axially aligned with and longitudinally spaced-apart from the first generally cylindrical inner electrode so as to define a circumferential gap between facing ends thereof, the circumferential gap defining an ion inlet; an outer generally cylindrical electrode having a third length and disposed in a concentric overlapping arrangement with the first generally cylindrical inner electrode and with the second generally cylindrical inner electrode, the outer generally cylindrical electrode defining an ion outlet within a portion thereof, a space between the second generally cylindrical inner electrode and the outer generally cylindrical electrode defining a FAIMS analyzer region, an average ion flow path being defined through said FAIMS analyzer region between the ion inlet and the ion outlet; and, an actuator for relatively translating the outer generally cylindrical electrode relative to both the first generally cylindrical inner electrode and the second generally cylindrical inner electrode, so as to vary a length of the average ion flow path between the ion inlet and the ion outlet.

According to an aspect of the instant invention, there is provided a method for controllably varying specificity of a FAIMS-based ion separation, comprising: providing a FAIMS analyzer region having an ion inlet for introducing a flow of ions thereto and having an ion outlet for extracting a subset of the flow of ions that is selectively transmitted along an average ion flow path between the ion inlet and the ion outlet; introducing a first flow of ions into the FAIMS analyzer region via the ion inlet; selectively transmitting a subset of the first flow of ions along the average ion flow path through the FAIMS analyzer region; relatively translating the ion inlet relative to the ion outlet so as to provide an average ion flow path of a different length through the FAIMS analyzer region; and, transmitting ions of a second flow of ions along the average ion flow path of a different length.

According to an aspect of the instant invention, there is provided an apparatus for controllably varying specificity of a FAIMS-based ion separation, comprising: a FAIMS analyzer region defined between a first electrode surface and a second other electrode surface, the FAIMS analyzer region in communication with an ionization source for providing a flow of ions including a known ion, and with an ion outlet for extracting ions including the known ion from the FAIMS analyzer region, the first and second electrode surfaces for having an asymmetric waveform voltage applied thereacross for defining an average ion flow path for the known ion traversing therebetween; and, an actuator for controllably moving the first electrode surface relative to the second electrode surface for controllably varying the length of the average ion flow path.

BRIEF DESCRIPTION OF THE DRAWINGS

Exemplary embodiments of the invention will now be described in conjunction with the following drawings, in which similar reference numerals designate similar items:

FIG. 8b is a plan view of the plate of FIG. 8a;

FIG. 9a is a perspective view of an optional flat plate design, in which the plate is absent sharp edges adjacent the inter-analyzer opening;

FIG. 9b is an enlarged partial side cross-sectional view of the flat plate of FIG. 9a, showing the shape of the inter-electrode opening in greater detail;

FIG. 10a is a side view of a cylindrical geometry FAIMS including a long cylinder surrounding two shorter axially aligned cylinders, and having a source of ions proximate to a gap between the two shorter aligned cylinders;

FIG. 10b is a simplified end view of the FAIMS of FIG. 10a;

FIG. 13a is a cross sectional end view of a FAIMS in the form of three electrodes with curved adjacent surfaces, with approximate alignment of the ion inlet, the inter-analyzer opening and the ion outlet;

FIG. 13b is a cross sectional end perspective view of the FAIMS of FIG. 13a with approximate alignment of the ion inlet, the inter-analyzer opening and the ion outlet;

FIG. 14a is a cross sectional end perspective view of the FAIMS of FIG. 13a with a displacement of distance A between the ion inlet and the inter-analyzer opening and between the inter-analyzer opening and the ion outlet;

FIG. 14b is a cross sectional end perspective view of the FAIMS of FIG. 13a with a displacement of distance A between the ion inlet and the inter-analyzer opening and between the inter-analyzer opening and the ion outlet, and showing ions flowing along an average ion flow path between the ion inlet and the ion outlet

DESCRIPTION OF EMBODIMENTS OF THE INVENTION

Figure 1:
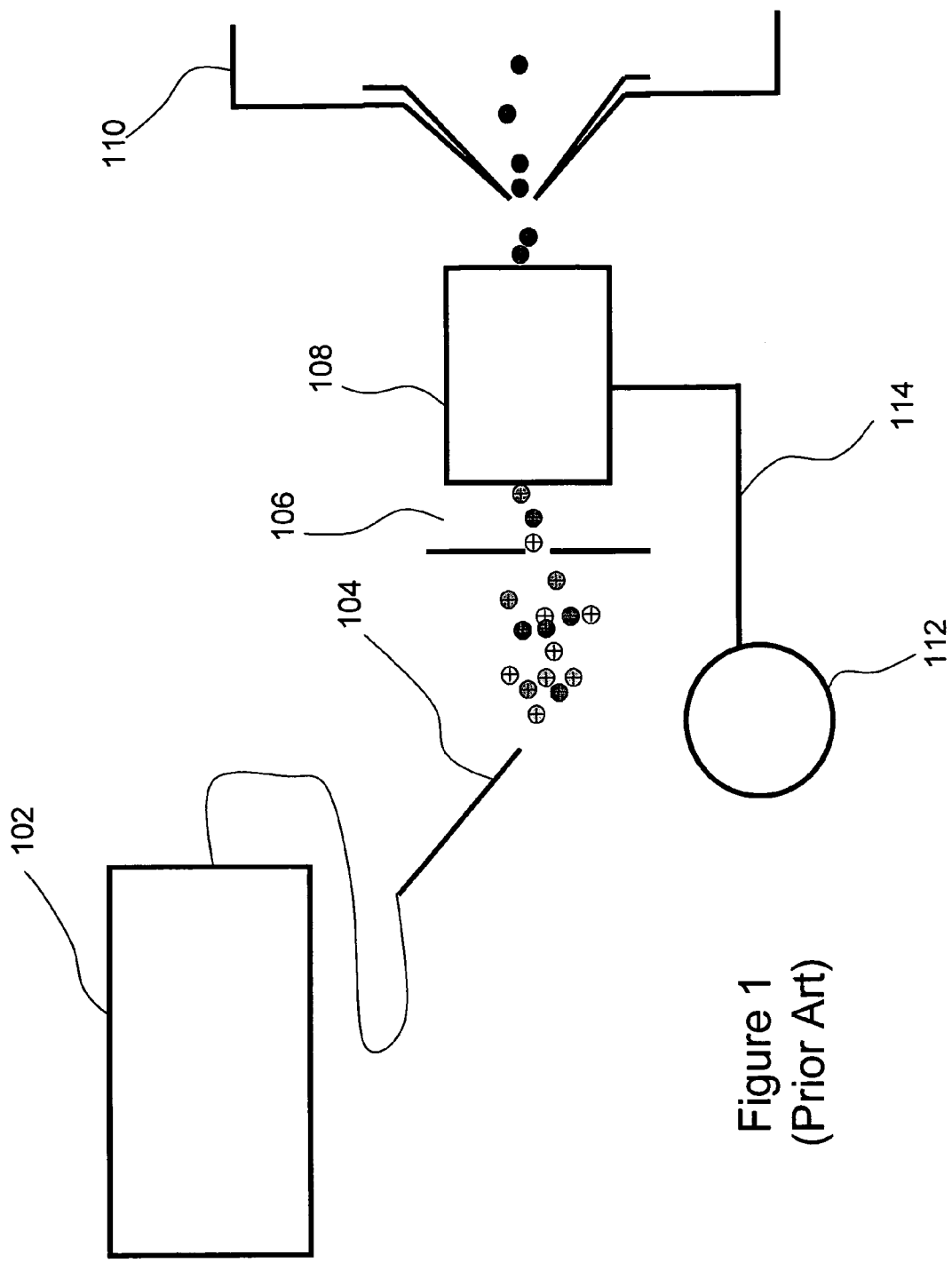
FIG. 1 is a simplified block diagram showing a prior art tandem arrangement including an ion source, a FAIMS, and a mass spectrometer.

The following description is presented to enable a person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and the scope of the invention. Thus, the present invention is not intended to be limited to the embodiments disclosed, but is to be accorded the widest scope consistent with the principles and features disclosed herein. Throughout the detailed description and in the claims that follow, the following terms shall be accorded the definitions as follows. An average ion flow path is defined as the net trajectory of an ion as a result of a carrier gas flow through the analyzer region, although the individual ion also experiences an oscillatory motion between the electrodes as a result of the applied asymmetric waveform voltage.

Throughout much of the following discussion it is assumed that the FAIMS electrodes are operating at atmospheric pressure, but the discussion is equally applicable at pressures below ambient atmospheric pressure and at pressures exceeding ambient atmospheric pressure. Furthermore, because ion separation and ion transmission in FAIMS is susceptible to changes in temperature it is desirable to operate FAIMS at a selected temperature setting. For example, a rise in temperature leads to a decrease in the number density of the gas (N, molecules per cc) and therefore the operating electric field (E/N) increases with rising temperature. Similarly an increase in gas pressure increases N and therefore decreases the effective E/N conditions. In order that experiments give consistent results when repeated, it is assumed that the temperatures and pressures are maintained at selected conditions, within selected tolerance limits.

It is also assumed that the physical conditions in the analyzer region of FAIMS do not significantly change the CV of the transmission of the ion of interest while it is passing through the analyzer region to a degree that prevents its transmission. For example, if conditions in different areas of the analyzer region differ substantially, those ions that are initially being successfully transmitted near the ion inlet region likely are lost to the electrode walls at a later time during their passage through the FAIMS analyzer region. This occurs, for instance, when conditions near the ion inlet are in a balanced state for a selected ion type, and the selected ion type is being transmitted near the ion inlet, but at a location elsewhere in the analyzer region the conditions are sufficiently different that the same selected ion type is migrating to the electrode walls and is being lost. Temperature, pressure, composition of the carrier gas and spacing between the electrodes, are a few non-limiting examples of the physical conditions, assuming constant applied voltages, that affect the CV of transmission of an ion. For example, a substantial difference in the electrode spacing near the ion inlet and near the ion outlet results in the field E/N near the inlet and near the outlet being different from each other. In some instances, moderate changes are beneficial for improving the resolution, or specificity, of ion separation, but larger changes that the ion experiences for longer times may result in complete loss of transmission of the ion. The term specificity is intended to describe the number of different ion types actually transmitted through a FAIMS device relative to the number of different ion types that are introduced via an ion inlet of the FAIMS. High specificity indicates that few or only one type of ion is actually being transmitted through the FAIMS, whereas low specificity indicates that many or all types of ion are actually being transmitted through the FAIMS. Of course, ion transmission efficiency may vary significantly with ion type, or may be relatively constant for different ion types. Thus, a total ion transmission mode (TITM) is by definition a low specificity mode of operation in which at least some fraction of many or all types of ions that are introduced via an ion inlet are transmitted through the FAIMS device to an ion outlet.

Referring now to FIG. 1, shown is a simplified block diagram of a prior art tandem arrangement including a condensed phase separation system 102, an ionization source 104, an ion desolvation region 106, a FAIMS 108, and a mass spectrometer 110. A power supply 112 applies voltages including an asymmetric waveform voltage and a compensation voltage to not illustrated electrodes of the FAIMS 108 via electrical connection 114. In FIG. 1 the ionization source 104 is shown, by way of non-limiting example, in the form of an electrospray ionization source. However, many other suitable ion sources are known, including photoionization sources, APCI sources, atmospheric pressure MALDI, radioactivity based sources, corona discharge sources, and other rf-based discharge sources, to name just a few non-limiting examples. The components 104, and 106 optionally are at elevated temperature to assist in desolvation of the ions, whereas 102, 108, and 110 are optionally at room temperature.

Referring still to FIG. 1, sample is provided from the condensed phase separation system 102 to ionization source 104. Ions produced from the sample are introduced into FAIMS 108 via desolvation region 106, and are separated according to the FAIMS principle. Ions that are transmitted through FAIMS 108 then travel to mass spectrometer 110 to be analyzed further or detected.

Figure 2:
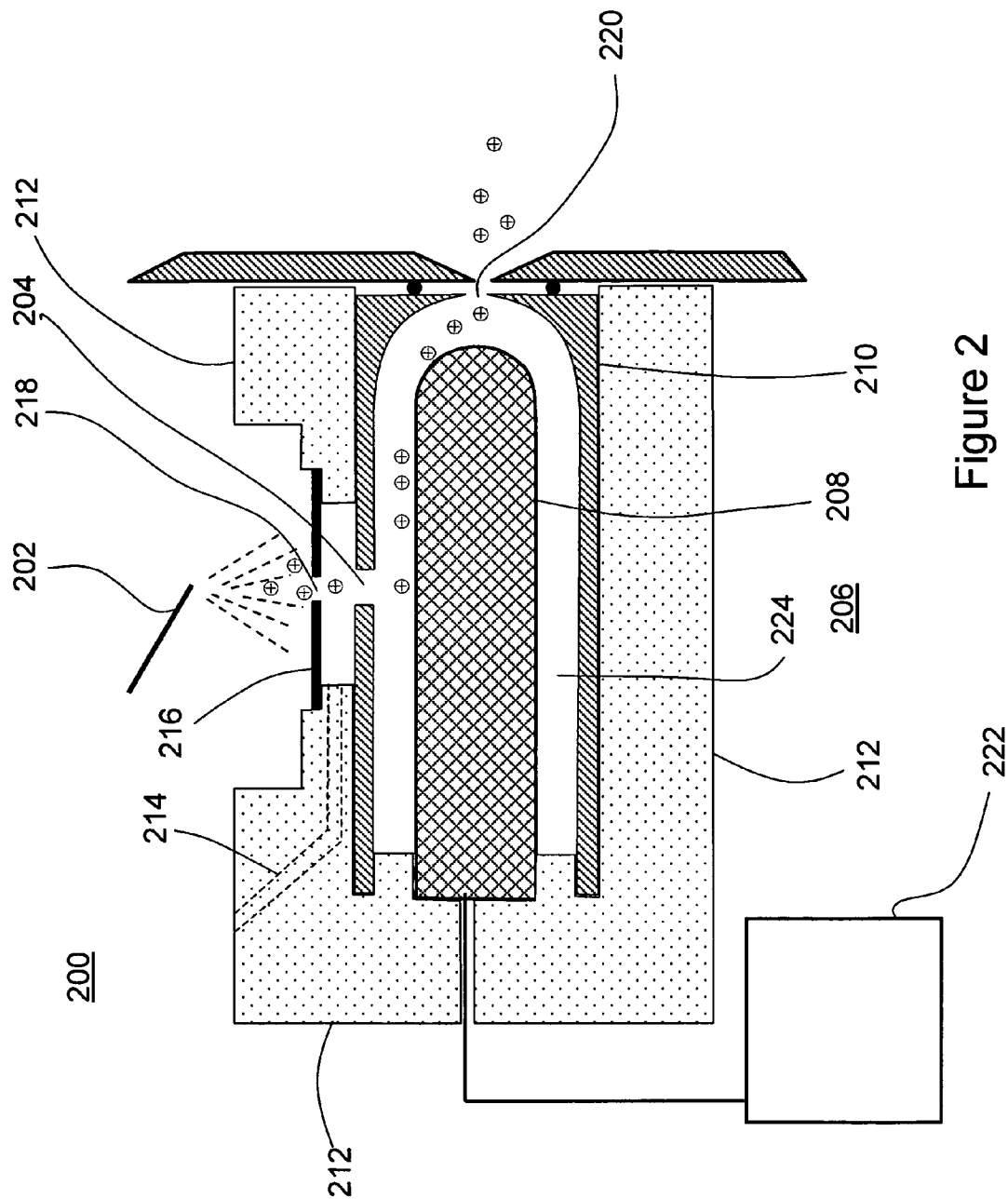
FIG. 2 is a longitudinal cross-sectional view of an electrospray ion source disposed in fluid communication with an ion inlet of a FAIMS.

Referring now to FIG. 2, shown is a longitudinal cross-sectional view of an ESI-FAIMS-MS tandem system, shown generally at 200. An electrospray ionization needle 202 is disposed in fluid communication with an ion inlet 204 of a FAIMS 206. The inner electrode 208 and the outer electrode 210 are supported in a spaced-apart arrangement by an insulating material 212 with high dielectric strength to prevent electrical discharge. Some non-limiting examples of suitable materials for use as the insulating material 212 include Teflon™ and PEEK. A passageway 214 for introducing a curtain gas is shown by dashed lines in FIG. 2, but often is omitted in later figures for simplicity of interpretation of the figures.

In FIG. 2, the ions are formed near the tip of electrospray needle 202 and drift towards a curtain plate 216. The curtain gas, introduced below the curtain plate 216 via the passageway 214, divides into two portions, one of which flows through an aperture 218 in the curtain plate 216, so as to prevent neutrals and droplets from entering the curtain plate aperture 218. Ions are driven against this flow of gas by a voltage gradient that is established between the needle 202 and the curtain plate 216. A field generated by a voltage difference applied between the curtain plate 216 and the FAIMS outer electrode 210 pushes ions that pass through the aperture 218 in the curtain plate 216 towards the ion inlet 204 of FAIMS 206. The second portion of the curtain gas flows into the ion inlet 204 and carries the ions along the length of the FAIMS electrodes to an ion outlet 220, and into a not illustrated mass spectrometer or other post-FAIMS analyzer/detector.

A high voltage asymmetric waveform is applied by electrical controller 222 to the inner electrode 208 of FAIMS 206, to produce an electric field that causes ions within an annular space between the inner electrode 208 and the outer electrode 210, which annular space is referred to as the analyzer region 224, to oscillate between the inner electrode 208 and the outer electrode 210. The waveform is generated in such a way to cause the ions to move in a first direction in a strong field for a short time, followed by motion in the other direction in a weaker field for a longer time. Absent any change in ion mobility between the high field and low field portions of this applied asymmetric waveform, after each cycle of the waveform the ion returns to its original position relative to the surface of the electrodes, without consideration of diffusion or ion-ion repulsion. In practice however, the mobility of many ions is different in strong and weak electric fields and for these ions the ion's position after one cycle of the waveform is not identical to its starting position relative to the electrode surfaces. A second, direct current voltage, which is referred to as the compensation voltage (CV), is applied to eliminate or compensate for this change of position. If the compensation voltage is of a magnitude that eliminates or compensates for the change of position that otherwise occurs absent the compensation voltage, the ion returns to the same relative location after each cycle of the waveform. Thus the ion does not migrate towards one or the other of the electrodes, and is transmitted through FAIMS 206. Other ions, for which the compensation voltage is too high or too low to compensate for the net displacement of the ion relative to the electrodes during one cycle of the waveform, drift towards an electrode and are unable to pass through FAIMS 206.

Still referring to FIG. 2, the cylindrical electrode geometry also permits ion focusing of the ion for which the asymmetric waveform voltage and compensation voltages are appropriate for transmission through FAIMS. This ion focusing mechanism means that ions, for which the compensation voltage exactly balances the change in position noted above, do not travel parallel to the walls of the electrodes as they are transported by the gas along the analyzer region 224. Under conditions of focusing, the ions that were originally near the electrode walls migrate to an optimum radial location between the electrodes. The ion cloud therefore tends to be located around this optimum radial location, thus 'focusing' the ions into a band within the space between the electrodes. Of course this cloud occupies a finite amount of space because the focusing is not strong and because diffusion, ion-ion electrostatic repulsion and other mechanical and chemical activity, including turbulence of the gas, tends to cause the ion cloud to spread out in space. At equilibrium the forces expanding the cloud are balanced by the focusing action of the electric fields in the analyzer region of FAIMS. This focusing effect is a result of the gradient of electric field E/N between the electrodes. In this example the gradient is generated because the electrodes are of cylindrical geometry, one of the possible physical geometries of electrodes that gives rise to non-constant E/N in space between the electrodes.

Two approaches are discussed for operating FAIMS 206 in total ion transmission mode. In a first approach the asymmetric waveform is deactivated and the inner electrode 208 and the outer electrode 210 are held at a same voltage. In a not illustrated second approach the asymmetric waveform is deactivated and the inner electrode 208 is retracted, or translated, so that the tip of the hemispherical end of the inner electrode 208 is no longer between the ion inlet 204 and the ion outlet 220. The voltages applied to the inner electrode 208 and to the outer electrode 210 are established empirically, to produce optimized ion transmission. In both of these approaches the mixture of ions that enters through ion inlet 204 is not separated by the FAIMS mechanism, and some of the non-separated mixture of ions exits through the ion outlet 220. The extent to which the ions are transmitted is influenced also by other mechanisms for relative selectivity of ion transmission, for example the relative rates of loss of various types of ions via diffusion. It is also important to note that the ion focusing properties of FAIMS are not operative absent the asymmetric waveform, since the variation in E/N in the radial direction is not sufficient for focusing, so that the ions are lost by mechanisms that include diffusion and ion-ion electrostatic mutual repulsion. Unfortunately, when operating in this optional non-separating mode, the length of the ion path between the ion inlet 204 and the ion outlet 220 is long, and the efficiency of transmission of the ions between the ion inlet 204 and the ion outlet 220 is low.

Figure 3:
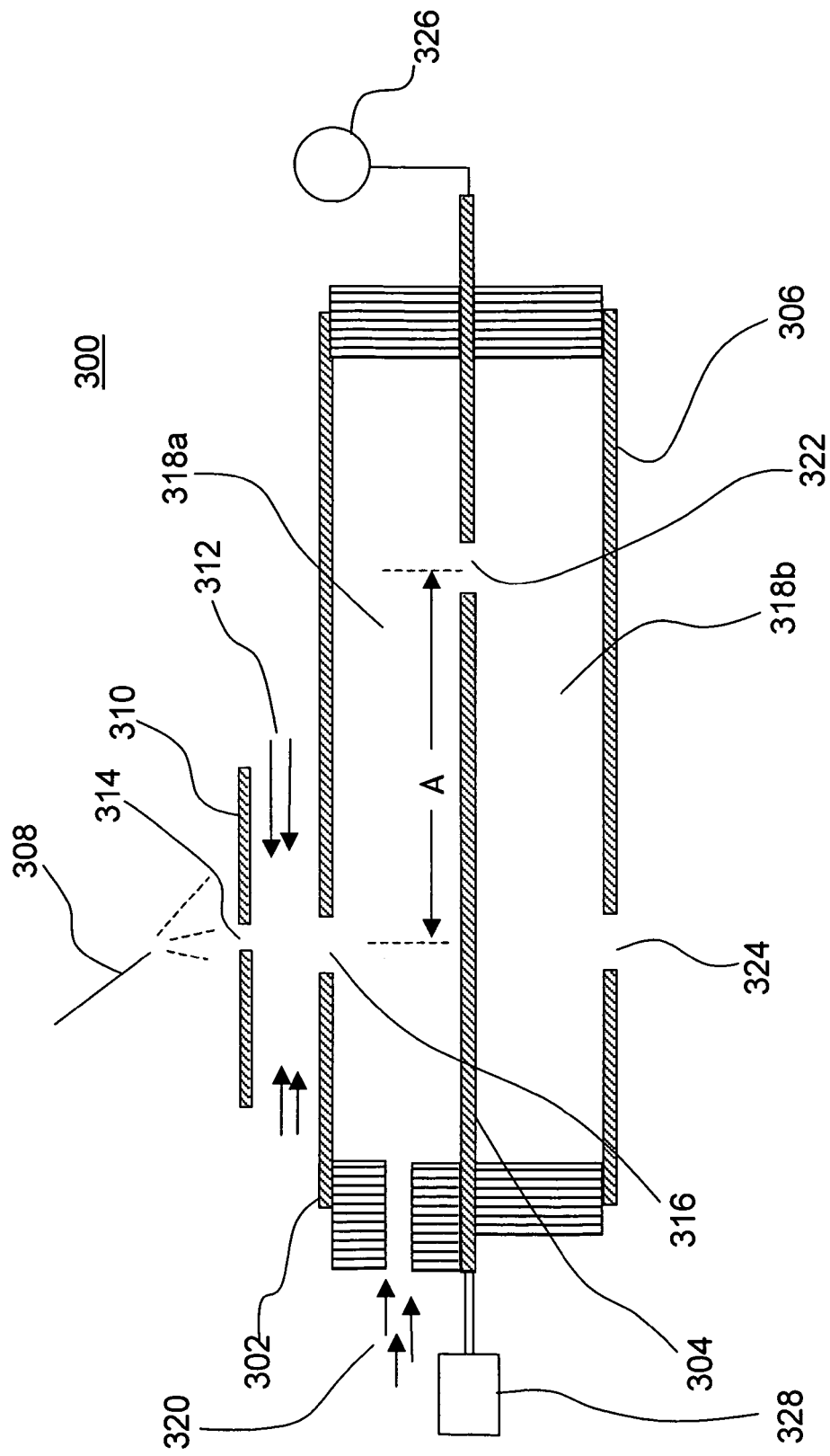
FIG. 3 is a longitudinal cross-sectional view of a parallel-plate geometry FAIMS, with a displacement of A between the openings in the top and middle plates and between the openings in the middle and lower plates.

FIG. 3 is a longitudinal cross-sectional view of a parallel plate FAIMS 300 including three stacked plates 302, 304 and 306, disposed in a spaced-apart relationship. The plates 302, 304 and 306 are stacked along a first direction, referred to as the stacking direction, such that a first electrode surface along plate 302 faces one side of the intermediate electrode plate 304, and a second electrode surface along plate 306 faces a side of the intermediate electrode plate 304 that is opposite the one side. Ions that are produced by ion source 308 drift along the first direction toward a curtain plate 310. A flow of a curtain gas 312, introduced below the curtain plate 310, divides into two portions, one of which flows outwardly through an aperture 314 in the curtain plate 310, so as to prevent neutrals and droplets from entering the curtain plate aperture 314. Ions are driven against this flow of gas by a voltage gradient that is established between the ion source 308 and the curtain plate 310. A field generated by a voltage difference between the curtain plate 310 and the FAIMS plate 302 pushes ions that pass through the aperture 314 in the curtain plate 310 towards the ion inlet 316 of FAIMS 300. The second portion of the curtain gas flows into the ion inlet 316 and carries the ions along the length of the FAIMS electrodes through the analyzer region 318a, along a second direction that is normal to the first direction. A second carrier gas flow 320 is optionally provided to assist in carrying the ions along the analyzer region 318a.

The ions travel along an average ion flow path, as is described hereinbelow. In particular, the ions travel an approximate distance along the average ion flow path indicated as "A" from the inlet 316 to an orifice, referred to as inter-analyzer aperture 322. The ions are carried by the flow of gas through the inter-analyzer aperture 322 into a second analyzer region 318b, and travel a second approximate distance "A" along the average ion flow path to the ion outlet 324. Accordingly, the inter-analyzer aperture defines a transition point, for changing the direction of ion flow along the average ion flow path. Since the asymmetric waveform and dc offset voltage is applied to the plate 304 from power supply 326, and assuming that the distance between plate 302 and 304 and between plate 304 and 306 are approximately equal, both analyzer regions 318a and 318b operate to separate ions in a substantially equivalent way. Optionally, to improve ion separation resolution, slightly different conditions are imposed in these analyzer regions 318a and 318b, for instance by varying electrode spacing or by application of different dc voltages to plates 302 and 306.

Figure 4:
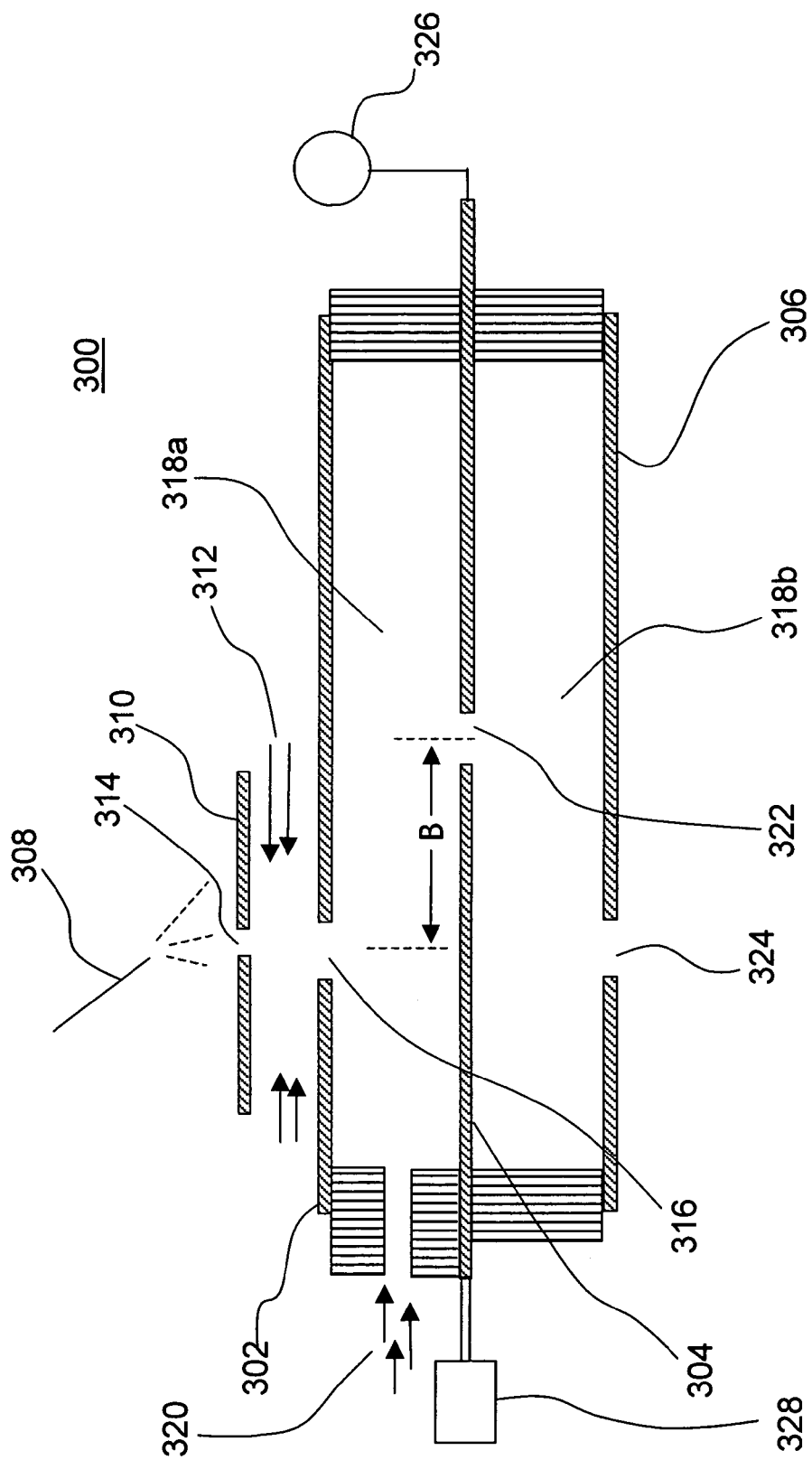
FIG. 4 is a longitudinal cross-sectional view of the FAIMS of FIG. 3 with a displacement of B between the openings in the top and middle plates and between the openings in the middle and lower plates.

FIG. 4 is a longitudinal cross-sectional view of the FAIMS of FIG. 3, with the inter-analyzer aperture 322 located at a distance "B" from the ion inlet 316. This system is designed such that the position of the inter-analyzer aperture 322 is selectable relative to the ion inlet 316 and the ion outlet 324. For instance, an actuator 328 is provided for translating the intermediate electrode plate 304 along the second direction, so as to translate the transition point as defined by the inter-analyzer aperture 322, and thereby controllably vary a length of the average ion flow path. The actuator 328 is optionally one of manually operable and automatically operable. For instance, the actuator 328 optionally includes a thumb-screw, an adjustable wheel or knob, or some other manually operable control mechanism for supporting manual adjustment of the inter-analyzer aperture 322 position. Alternatively, the actuator 328 optionally includes a motor that drives the electrode 304 in one of a continuous and a stepped manner via a linkage member.

FIG. 4 illustrates that this arrangement of electrodes provides the benefit of an adjustable ion transit time, allowing the separation of ions and the efficiency of ion transmission to be established empirically by adjusting the position of the inter-analyzer aperture 322 relative to the ion inlet 316 and the ion outlet 324. If the gas flow rate is sufficiently high that the ion residence time is too short to achieve a desired degree of separation of one type of ion from another type of ion, the distance B between the ion inlet 316 and the inter-analyzer aperture 322 is increased, for instance to distance "A" as shown previously in FIG. 3. Optionally this distance is adjusted by mechanical horizontal translation of plate 304, however, those knowledgeable in the field will appreciate that this distance is readily adjusted in many different ways.

In principle, the device as configured in either of FIG. 3 and FIG. 4 optionally is operated in a non-separating TITM by removal of the asymmetric waveform and the dc compensation voltage. In this condition the device shown in FIG. 3 and FIG. 4 passes a mixtures of ions without active FAIMS-based separation however the mixture of ions is required to travel some distance between the closely spaced electrodes/plates and ion transmission efficiency from the ion source to the post-FAIMS detector/analyzer is expected to be reduced.

Figure 5:
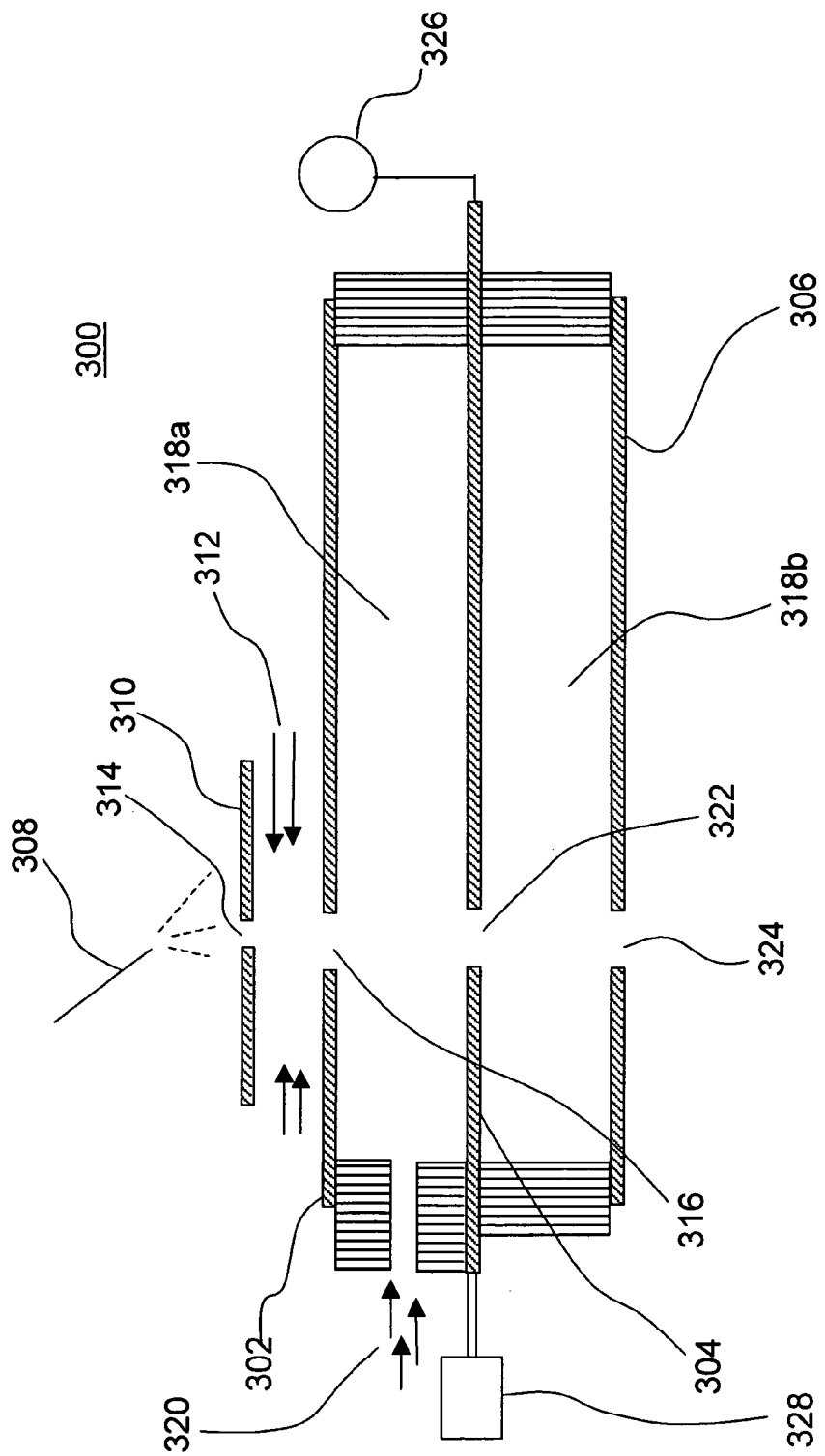
FIG. 5 is a longitudinal cross-sectional view of the FAIMS of FIG. 3 with the openings in the top, middle and lower plates vertically aligned.

It is an unforeseen benefit of the system shown in FIG. 3 and FIG. 4 that the distances "A" or "B" are optionally reduced effectively to zero, as shown in FIG. 5. This also has the advantage of de-activating the FAIMS, and thereby providing a readily available mechanism for total ion transmission mode (TITM). Referring now to FIG. 5, by aligning the ion inlet 316, the inter-analyzer aperture 322 and the ion outlet 324, the ion separation mechanism of FAIMS is minimized, so that the majority of ions passing through ion inlet 316 exit through the ion outlet 324. The transmission of ions is significantly higher with the alignment of the ion inlet 316, the inter-analyzer aperture 322 and the ion outlet 324, than if the inter-analyzer aperture 322 remained located at distance "A" or "B" as shown in FIGS. 3 and 4 with the asymmetric waveform and the dc compensation voltage removed. Furthermore, in FIG. 5 the ion transmission optionally is further controlled by removal of the applied asymmetric waveform and replacement of the dc voltages applied to plates 302, 304 and 306 with dc voltages that are determined empirically to maximize the efficiency of transport of ions from the ion inlet 316 to the ion outlet 324.

Still referring to FIG. 5, assuming the widths of the analyzer regions 318a and 318b are each 2 mm, the distance from the ion inlet 316 to the ion outlet 324 is now only 4 mm plus the thickness of the plate 304. The efficiency of transport of ions through this non-separating FAIMS is significantly higher than that of the system in the state shown in FIG. 3 or FIG. 4 operated in non-separating mode by removal of the waveform voltages, since for example in the system of FIG. 3 the ions travel twice the distance "A". Additionally, when operating in a non-separating mode the ions are difficult to transport unless the dc voltages applied to the plates 302, 304 and 306 are substantially equal, since any voltage difference adds an electric field that tends to force the ions to collide with one of the plates. Referring again to FIG. 5, the dc voltages applied to the plates 302, 304 and 306 are helpful in pulling the ions through the three co-aligned openings, namely ion inlet 316, inter-analyzer aperture 322 and ion outlet 324.

Although the system shown in FIGS. 3 through 5 include three separate electrode plates 302, 304 and 306, optionally the plates 302 and 306 are replaced by a single formed electrode having a generally "C-shaped" structure, such that a first electrode surface portion of the formed electrode faces one side of the intermediate electrode plate 304, and a second electrode surface portion of the same formed electrode faces a side of the intermediate electrode plate 304 that is opposite the one side.

Of course, the parallel plate version of FAIMS that is shown in FIGS. 3 through 5 is known to lack focusing properties, other than at the edges of the plates, in the absence of temperature gradients or any other conditions creating an electric field gradient between the electrodes. Fortunately, when temperature conditions between the parallel plate electrodes are established to mimic the E/N gradient in cylindrical geometry FAIMS, a beneficial focusing effect occurs. The transmission of ions at a fixed CV requires control of the temperature in the analyzer region, such that the CV conditions for transmission of a selected ion do not change significantly as the ion travels along the space between the electrodes. By controlling the temperature of the carrier gas and by controlling the temperature of each of the electrodes to create a temperature gradient in the gas between the electrodes, ion focusing conditions are established in the parallel plate version of FAIMS.

Figure 6:
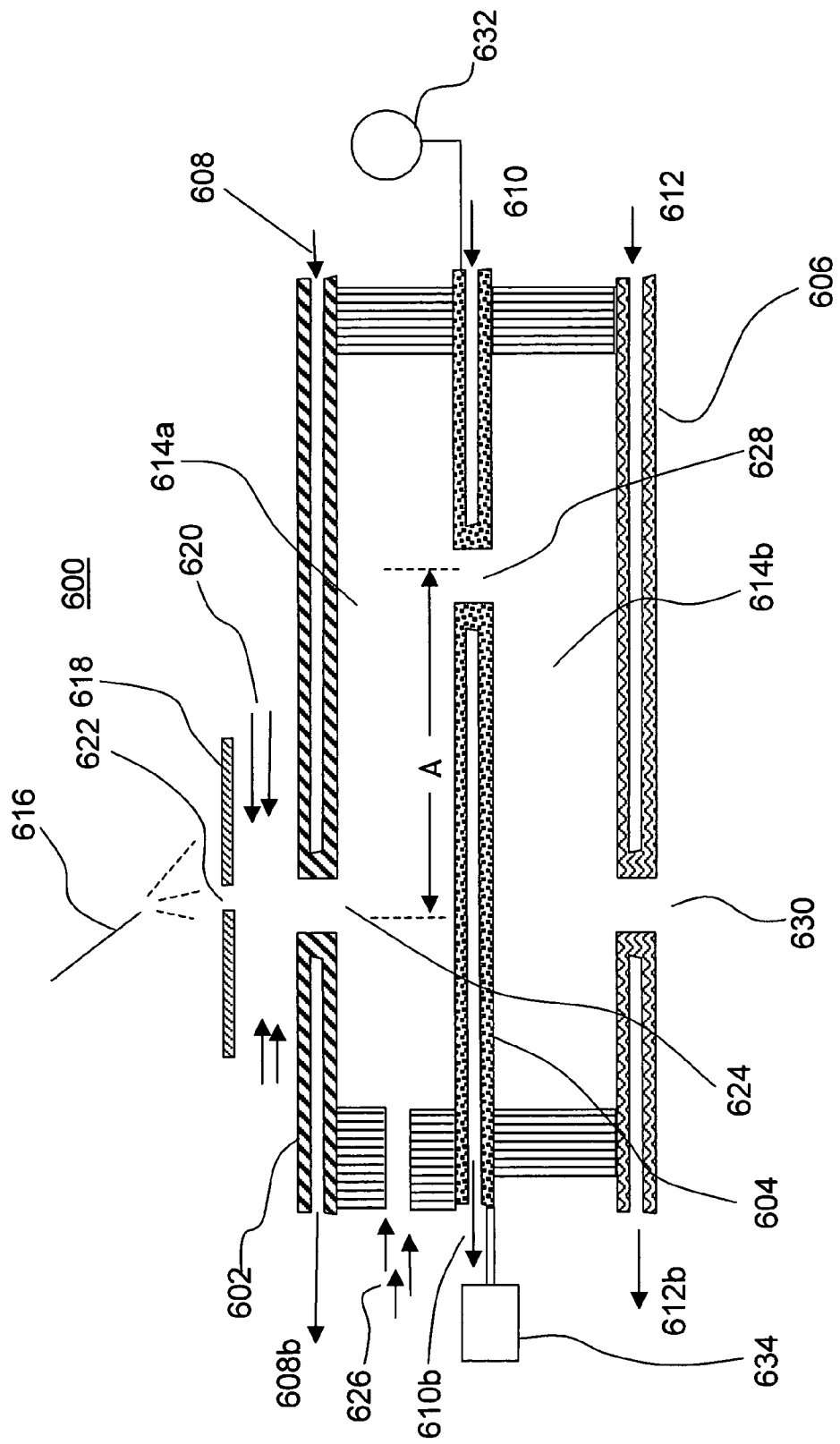
FIG. 6 is a longitudinal cross-sectional view of a parallel-plate geometry FAIMS including a temperature controller for controlling the temperature of the three plates.

FIG. 6 illustrates a FAIMS system 600 similar to that shown in FIGS. 3 through 5, however a temperature controller is provided to control the relative temperatures of each of the three plates 602, 604 and 606. Three flows 608, 610 and 612 of a heating/cooling fluid, referred to more generally as a heat-exchange fluid, are delivered to channels in the plates 602, 604 and 606 respectively. The heat-exchange fluid passes through channels in the plate and exits from the three plates as flows 608b, 610b and 612b from plates 602, 604 and 606 respectively. Preferably these three heat-exchange fluid flows are circulated and temperature controlled independently. The heat-exchange fluid flows are used to adjust and stabilize the temperatures of the three plates, with the benefit of producing temperature gradients between the electrodes. The temperature gradient produces a gradient of E/N between the plates during application of the asymmetric waveform and dc offset voltages between the electrodes. The gradient of E/N is beneficially controlled to maximize the ion transmission through the analyzer regions 614a and 614b.

Referring still to FIG. 6, ions that are produced by ion source 616 drift toward a curtain plate 618. A flow of a curtain gas 620, introduced below the curtain plate 618, divides into two portions, one of which flows outwardly through an aperture 622 in the curtain plate 618, so as to prevent neutrals and droplets from entering the curtain plate aperture 622. Ions are driven against this flow of gas by a voltage gradient that is established between the ion source 616 and the curtain plate 618. A field generated by a voltage difference between the curtain plate 618 and the FAIMS plate 602 pushes ions that pass through the aperture 622 in the curtain plate 618 towards the ion inlet 624 of FAIMS 600. The second portion of the curtain gas flows into the ion inlet 624 and carries the ions along the length of the FAIMS electrodes through the analyzer region 614a. A second carrier gas flow 626 is optionally provided to assist in carrying the ions along the analyzer region 614a.

The ions travel along an average ion flow path, as is described hereinbelow. In particular, the ions travel an approximate distance along the average ion flow path indicated as "A" from the inlet 624 to an orifice in the intermediate electrode plate 604, which is referred to as inter-analyzer aperture 628. The ions are carried by the flow of gas through the inter-analyzer aperture 628 into a second analyzer region 614b, and travel a second approximate distance "A" along the average ion flow path to the ion outlet 630. Accordingly, the inter-analyzer aperture 628 defines a transition point, for changing the direction of ion flow along the average ion flow path. Since the asymmetric waveform and dc offset voltage is applied to the plate 604 from power supply 632, and assuming that the distance between plate 602 and 604 and between plate 604 and 606 are approximately equal, both analyzer regions 614a and 614b operate to separate ions in a substantially equivalent way. Optionally, to improve resolution, slightly different conditions are imposed in these analyzer regions 614a and 614b, for instance by electrode spacing variation or by application of different dc voltages to plates 602 and 606.

Figure 7:
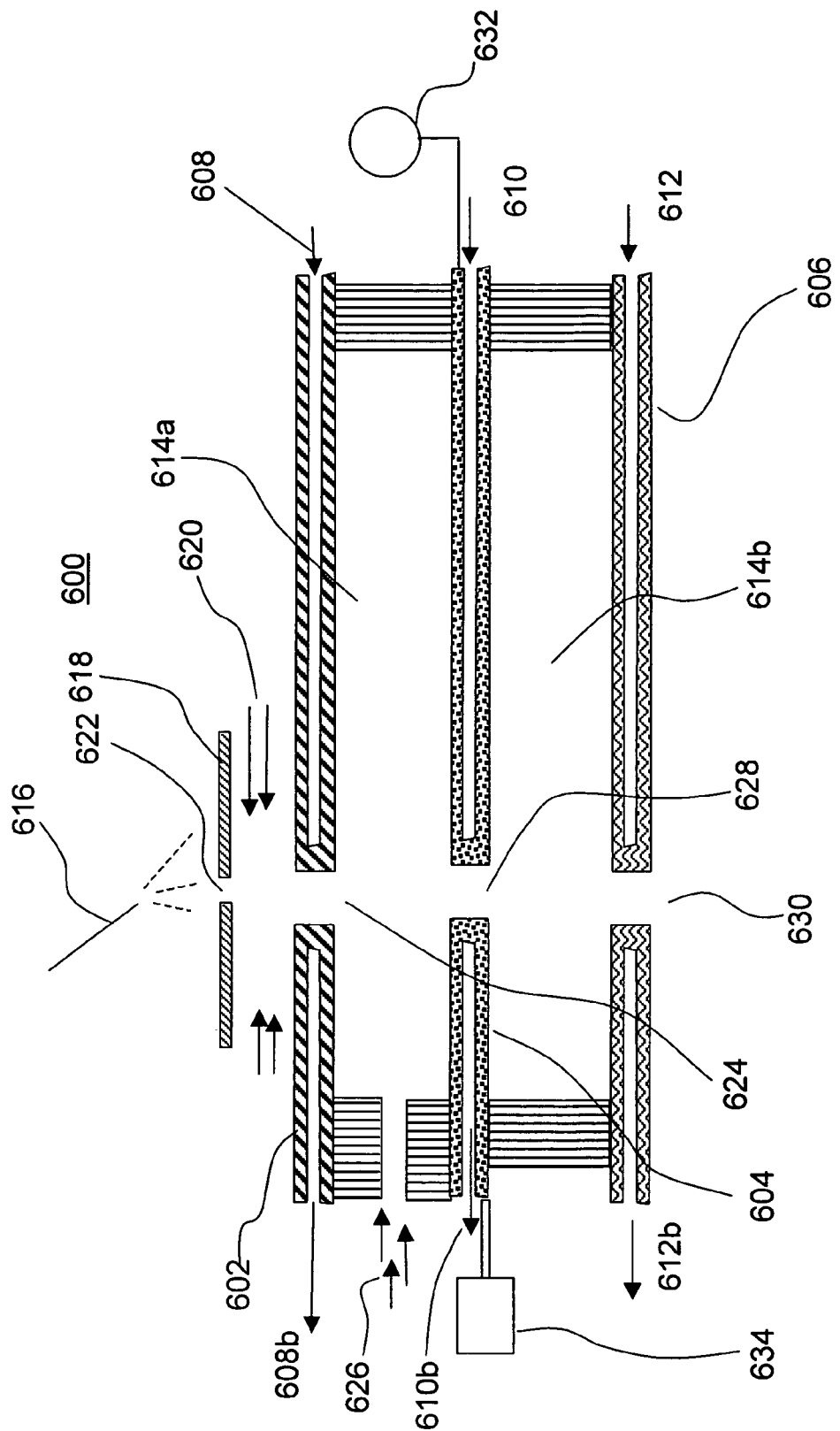
FIG. 7 is a longitudinal cross-sectional view of the FAIMS of FIG. 6 with the openings in the top, middle and lower plates vertically aligned.

FIG. 7 illustrates the same system that is shown in FIG. 6, but with the inter-analyzer aperture 628 located in alignment with the ion inlet 624 and the ion outlet 630. For instance, an actuator 634 is provided for translating the intermediate electrode plate 604 along a direction parallel to the plates 602 and 606, so as to translate the transition point as defined by the inter-analyzer aperture 628, and thereby controllably vary a length of the average ion flow path. The actuator 634 is optionally one of manually operable and automatically operable. For instance, the actuator 634 optionally includes a thumb-screw, an adjustable wheel or knob, or some other manually operable control mechanism for supporting manual adjustment of the inter-analyzer aperture 628 position. Alternatively, the actuator 634 optionally includes a motor that drives the intermediate electrode plate 604 in one of a continuous and a stepped manner via a linkage member. With alignment of the three openings the ions that are delivered to ion inlet 624 pass without separation to the ion outlet 630, with the device acting in total ion transmission mode. In this mode of operation, it is preferable that the asymmetric waveform be deactivated, and dc potentials placed on all three plates 602, 604 and 606. The dc potentials are selected to maximize the efficiency of transmitting ions from ion inlet 624 to ion outlet 630.

Figure 8A:
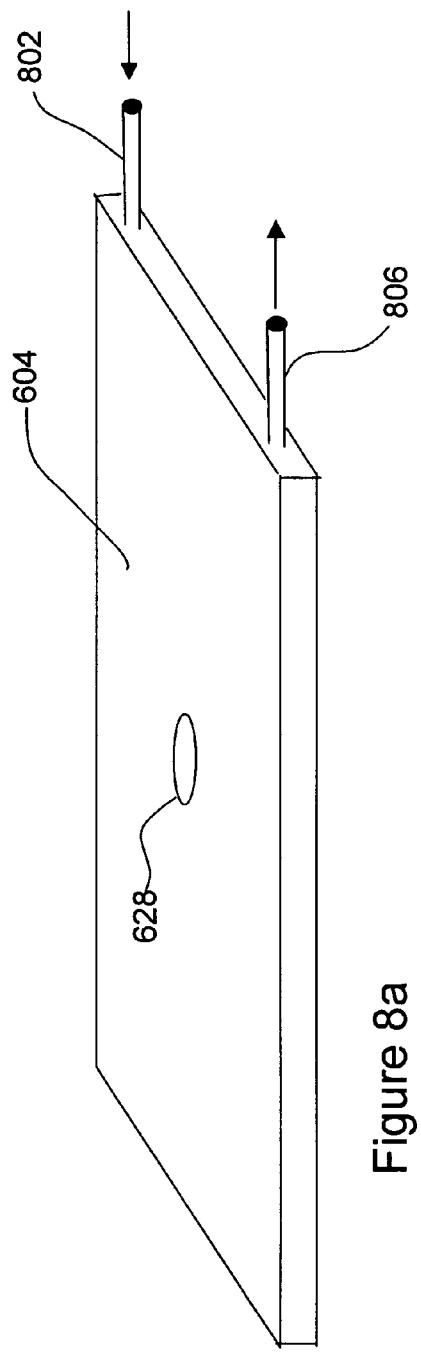
FIG. 8a is a perspective view of one of the plates of the FAIMS of FIG. 6, showing the heat-exchange fluid circulation system in greater detail.
Figure 8B:
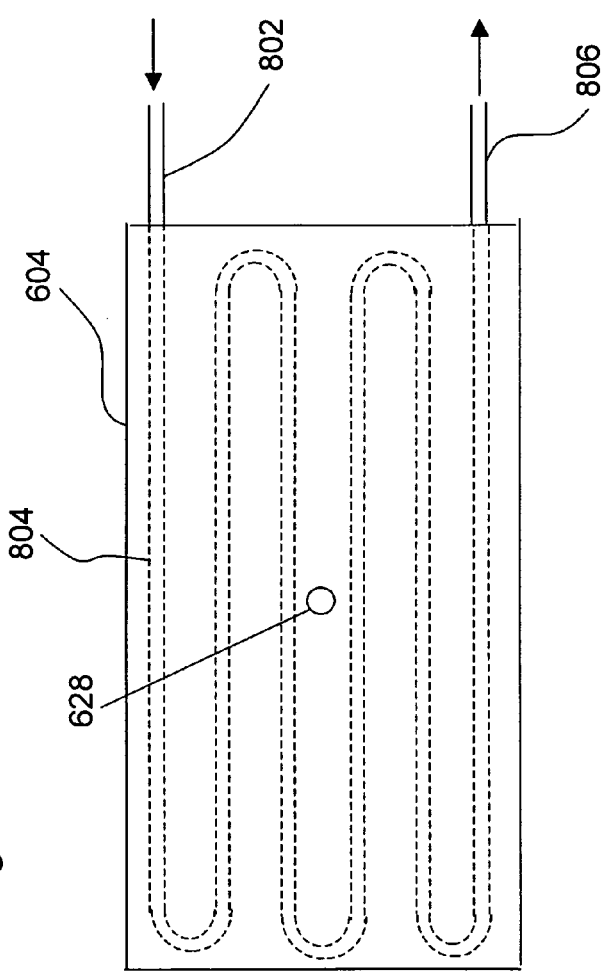

FIGS. 8a and 8b illustrate one approach to passing a heat-exchange fluid through the plates 602, 604 or 606 of the system shown in FIG. 6 and FIG. 7. In the specific example that is shown in FIGS. 8a and 8b, a flow of the heat-exchange fluid enters plate 604 through a fluid inlet 802, and having passed along a channel 804 within the plate, the fluid exits from fluid exit port 806. Optionally the plate is heated by resistive elements or thermoelectric elements embedded into the plate. Optionally, similar structure is provided for controlling temperature of plates 602 and 606.

Referring now to FIG. 9a and FIG. 9b, shown is a perspective view and an enlarged partial side cross-sectional view, respectively, of an optional flat plate design, in which the plate 902 is absent sharp edges adjacent the inter-analyzer aperture 908. In the specific example that is shown in FIG. 9a, a flow of a heat-exchange fluid enters plate 902 through a fluid inlet 904, and having passed along a not illustrated channel within the plate, the heat-exchange fluid exits from fluid exit port 906. The periphery of inter-analyzer aperture 908 is curved so as to smoothly join the upper and lower surfaces of plate 902. The absence of sharp edges on plate 902 adjacent the inter-analyzer aperture 908 beneficially guides ions and gas flow through the inter-analyzer aperture 908 and reduces the possibility of electrical arcing between the plate 902 and adjacent electrode surfaces.

The embodiments of the present invention that have been discussed with reference to FIGS. 3 through 7 beneficially provide a very thin and relatively flat FAIMS device, which is readily positioned between a source of ions and the inlet of a post-FAIMS analyzer, such as for instance a mass spectrometer or further FAIMS devices. Advantageously, neither the ionization source nor the post-FAIMS analyzer is mechanically moved during the switching between separation mode and the non-separating TITM of FAIMS.

Figures 10A, 10B:
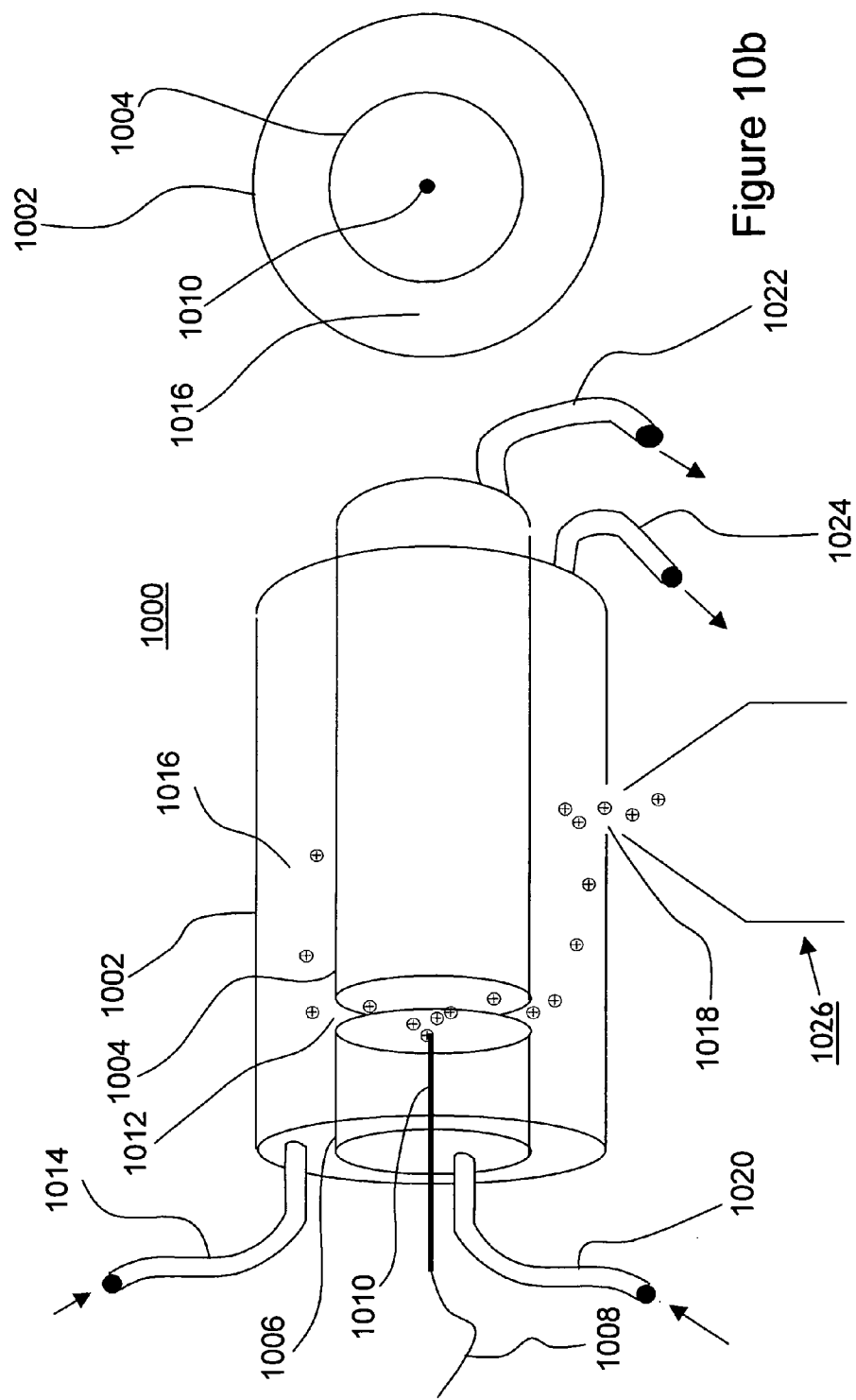

Referring now to FIGS. 10a and 10b, shown is a side view and a simplified end view, respectively, of a cylindrical geometry FAIMS 1000 including a long outer cylinder 1002 surrounding a first inner cylinder 1004 and a second inner cylinder 1006 that is axially aligned with the first inner cylinder 1004. In FIG. 10a, the long outer cylinder is transparent, so as to show more clearly the inner components including the first inner cylinder 1004 and the second inner cylinder 1006. Not illustrated electrically insulating material supports the first inner cylinder 1004 and the second inner cylinder 1006 relative to the long outer cylinder 1002, so as to maintain spacing therebetween.

A flow of liquid sample is provided through a sample delivery tube 1008 to the tip of an ESI source needle 1010. Ions are produced and pushed outward radially because of the high voltage applied to the ESI source needle 1010. Appropriate voltages applied to the shorter second inner cylinder 1006 and the long outer cylinder 1002 drive the ions outwardly in a radial direction away from the source needle 1010 and through a gap 1012 between the shorter second inner cylinder 1006 and the longer first inner cylinder 1004. In this example, the asymmetric waveform and dc offset compensation voltages are applied to the first inner cylinder 1004 through not-illustrated electrical connections.

Referring still to FIGS. 10a and 10b, the ions pass radially outward through the gap 1012 and are entrained in a flow of carrier gas that is supplied by carrier gas conduit 1014 to the annular space between the concentric second inner cylinder 1006 and the long outer cylinder 1002. The carrier gas flow transports the ions along the annular analyzer region 1016 from the gap 1012 to the ion outlet 1018. By application of appropriate asymmetric waveform voltage and dc voltages to the first inner cylinder 1004 and the long outer cylinder 1002, the ions are separated during transport along the analyzer region 1016. A flow of sampler gas provided to the sampler gas conduit 1020 serves to carry neutral molecules and solvent through the space inside of the longer first inner cylinder 1004, after which the gas and the entrained molecules exit from the system through a sampler gas exit conduit 1022. An exit flow of carrier gas is optionally transported out of carrier gas exit conduit 1024. The gas flows, that is to say, the flow through carrier gas conduit 1014, sampler gas conduit 1020, sampler gas exit conduit 1022 and carrier gas exit conduit 1024, are adjusted to ensure that a stream of carrier gas passes into the gap 1012 between the second inner cylinder 1006 and the first inner cylinder 1004. The stream of carrier gas that passes into the gap 1012 is moving in a direction opposite to that of the ions passing outwardly through the same gap 1012, and thus acts to help desolvate the ions and to prevent neutrals from the needle 1010 from contaminating the portion of the carrier gas flow that passes along the analyzer region 1016.

Referring still to FIG. 10a, there are two approaches to providing a non-separated mixture of ions to a post-FAIMS device 1026, such as for instance one of a mass spectrometer, a further FAIMS device, or an ion detector as some non-limiting examples. In a first approach the asymmetric waveform is deactivated and the first inner cylinder 1004 and the outer cylinder 1002 held at a same voltage. In a second approach the asymmetric waveform is deactivated and the first inner cylinder 1004 is retracted away from the second inner cylinder 1006 so that the end of the first inner cylinder 1004 is no longer between the ion source 1010 and the ion outlet 1018. In both of these approaches the mixture of ions produced by the ion source 1010 is not separated by the FAIMS mechanism, and some of the non-separated mixture of ions exits through the ion outlet 1018. Of course, other mechanisms for relative selectivity of ion transmission may still exist, for example if the relative rates of loss of various types of ions via diffusion are different. When operating in these optional non-separating modes, the pathway between the ion source 1010 and the ion outlet 1018 is long and the efficiency of transmission of the ions is not high.

Figure 11:
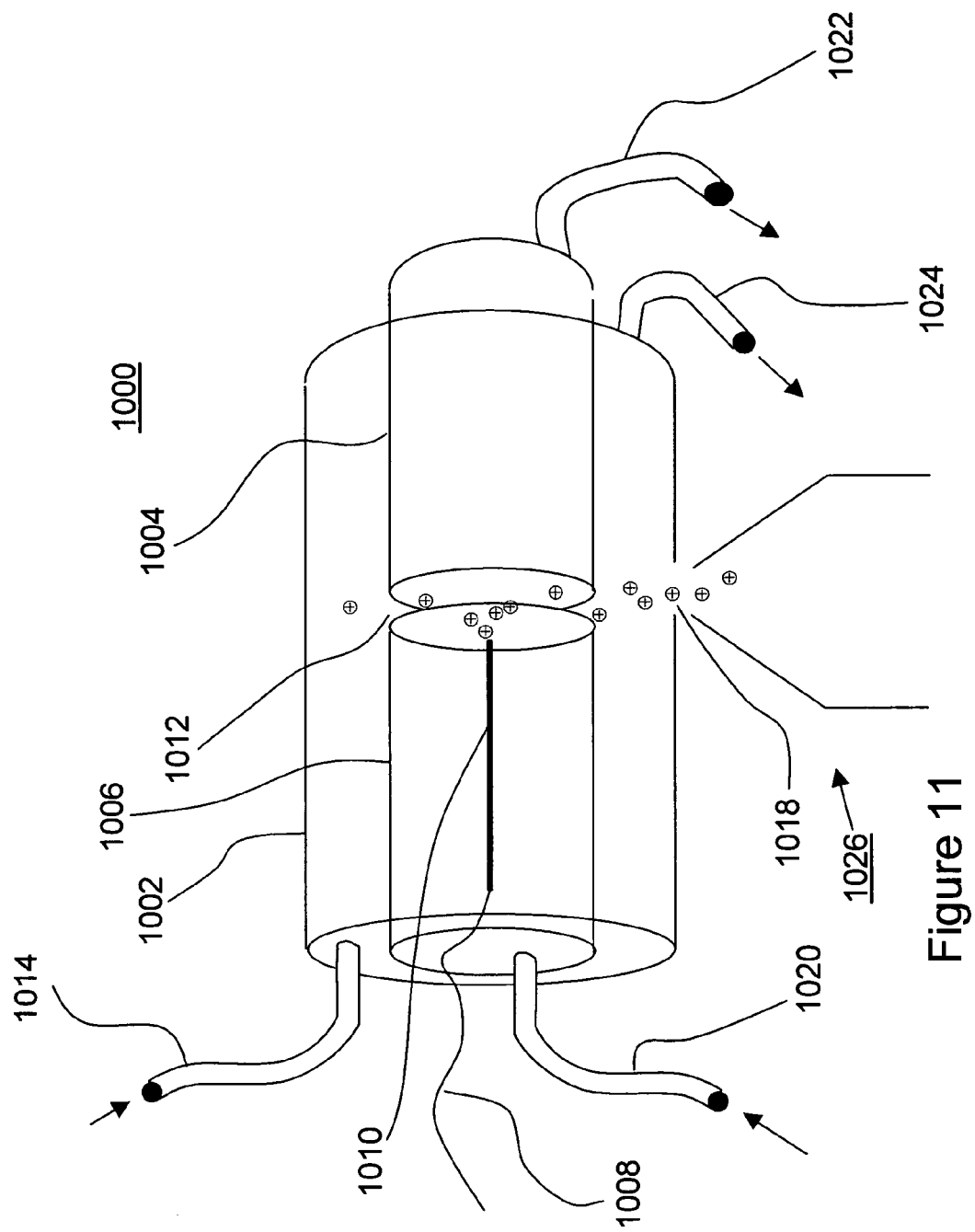
FIG. 11 is a side view of the FAIMS of FIG. 10a with the two shorter axially aligned cylinders translated longitudinally so that the gap between these cylinders is approximately adjacent to the ion outlet.

Referring now to FIG. 11, shown is a side view of the FAIMS of FIG. 10a with the first inner cylinder 1004 and the second inner cylinder 1006 translated longitudinally so that the gap 1012 between these cylinders is approximately adjacent to the ion outlet 1018. FIG. 11 illustrates the FAIMS system 1000 during non-separating, total ion transmission mode whereas FIG. 10a with the application of the asymmetric waveform and a dc compensation voltage illustrates the FAIMS system 1000 during the normal separating operating mode of FAIMS. The conversion between the non-separating and the normal operating mode is achieved via the translation of the first inner cylinder 1004, the second inner cylinder 1006, and the ionization source 1010, and via control of the above-mentioned applied voltages. To this end, a not illustrated actuator is provided. The not illustrated actuator is similar to the actuator 328 or 634 as described above. These components are moved so that the gap 1012 becomes aligned with the ion outlet 1018 in the outer cylinder 1002. Accordingly, the actuator is for moving synchronously the first inner cylinder 1004, the second inner cylinder 1006 and the ionization source 1010. The sample delivery tube 1008 must have provision to remain connected during this translation, and similarly the sample gas delivery conduit 1020 and the sampler gas exit conduit 1022 are flexibly connected to support such translational motion of the inner components of FAIMS system 1000.

In FIG. 11, a flow of liquid sample is provided through the sample delivery tube 1008 to the tip of the ESI source needle 1010. Ions are produced and pushed outward radially because of the high voltage applied to the ESI source needle 1010. Appropriate voltages applied to the shorter second inner cylinder 1006 and the long outer cylinder 1002 drive the ions outwardly in a radial direction away from the source needle 1010 and through the gap 1012 between the shorter second inner cylinder 1006 and the longer first inner cylinder 1004. In this example, the appropriate voltage is applied to the first inner cylinder 1004 through not-illustrated electrical connections.

Referring still to FIG. 11, the ions pass radially outward through the gap 1012 and travel to the ion outlet 1018 along an average ion flow path that is substantially perpendicular to the cylinder surfaces. Accordingly, the length of the average ion flow path is approximately equal to the size of the annular space between an outer surface of the first inner cylinder 1004 and an inner surface of the long outer cylinder 1002. The average ion flow path does not include a component along a direction that is parallel to the cylinder surfaces, and as such the ions are not separated according to the FAIMS principle.

Figure 12:
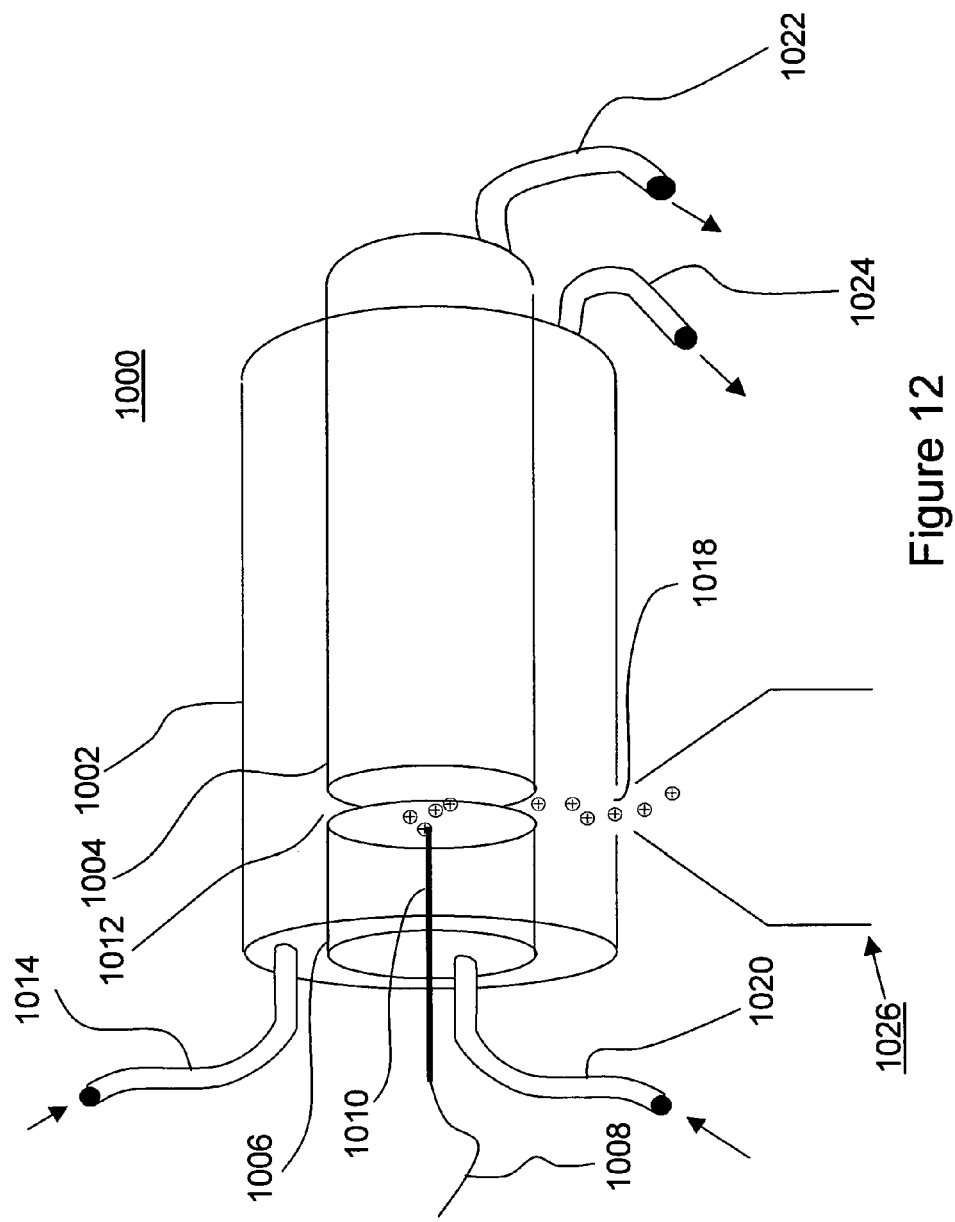
FIG. 12 is a side view of the FAIMS of FIG. 10a with the ion outlet proximate to the gap between the two shorter aligned cylinders.

Referring now to FIG. 12, shown is a side view of the FAIMS of FIG. 10a with the outer cylinder 1002 translated longitudinally so that the ion outlet 1018 is approximately adjacent to the gap 1012 between the first inner cylinder 1004 and the second inner cylinder 1006. FIG. 12 illustrates the FAIMS system 1000 during non-separating, total ion transmission mode whereas FIG. 10a with the application of an asymmetric waveform and a dc compensation voltage illustrates the FAIMS system 1000 during the normal separating operating mode of FAIMS. The conversion between the non-separating and the normal operating mode is achieved via the translation of the long outer cylinder 1002, as well as the post-FAIMS device 1026, such as for instance one of a mass spectrometer, a further FAIMS device, or an ion detector as some non-limiting examples. To this end, a not illustrated actuator is provided. The not illustrated actuator is similar to the actuator 328 or 634 as described above. These components are moved so that the ion outlet 1018 becomes aligned with the gap 1012 between the first inner cylinder 1004 and the second inner cylinder 1006. Accordingly, the actuator is for moving synchronously the long outer cylinder 1006, and the post FAIMS device 1026. Of course, translation of heavier or bulkier post FAIMS devices, such as for instance a mass spectrometer, limits the applicability of this approach. Smaller and more compact post FAIMS devices, such as for instance a lightweight ion detector or another FAIMS device, are better suited for this approach.

Referring still to FIG. 12, the ions pass radially outward through the gap 1012 and travel to the ion outlet 1018 along an average ion flow path that is substantially perpendicular to the cylinder surfaces. Accordingly, the length of the average ion flow path is approximately equal to the size of the annular space between an outer surface of the first inner cylinder 1004 and an inner surface of the long outer cylinder 1002. The average ion flow path does not include a component along a direction that is parallel to the cylinder surfaces, and as such the ions are not separated according to the FAIMS principle.

FIG. 11 and FIG. 12 show two ways of relatively moving the ion outlet 1018 relative to the gap 1012. In FIG. 11, only the inner components are translated, which reduces complexity. In contrast, FIG. 12 requires translation of the post-FAIMS device and therefore is more complex depending on the post-FAIMS device. For ease of use, minimization of the number of components that require movement is desired. Furthermore, movement of heavier components, such as for instance the post FAIMS device 1026, is to be avoided when possible.

FIGS. 13a and 13b illustrate a FAIMS system 1300, in which the FAIMS electrodes are cylindrical in geometry, thereby providing the beneficial effects of ion focusing when operating in the normal FAIMS ion separating mode. In addition, a single electrode within FAIMS 1300 is readily translatable between two positions, one position that provides a FAIMS separation and a second position in which FAIMS separation is absent. It is beneficial that the ionization source, which is not shown in FIGS. 13a and 13b, is not mechanically moved. It is also beneficial that most of the FAIMS device is not moved and that the post-FAIMS system, which also is not shown in FIGS. 13a and 13b, is not moved during the change of FAIMS to non-FAIMS operating mode.

Referring now to FIG. 13a, a stream 1302 of ions from a not-illustrated ionization source pass through an ion inlet opening 1304 in a first curved electrode 1306. The curved electrode 1306 is spaced apart from a first curved surface 1308 of an intermediate electrode 1310. The ions pass through an inter-analyzer aperture 1312 in the intermediate electrode 1310. A third curved electrode 1314 is adjacent to a second curved surface 1316 of the intermediate electrode 1310. The stream of ions passes through an ion outlet opening 1318 through the third electrode 1314, and the stream of transmitted ions 1404 is delivered to an optional further analyzer, for example one of a FAIMS, a drift tube IMS, and a mass spectrometer as non-limiting examples.

FIG. 13b is a cross-sectional end perspective view of the FAIMS 1300 of FIG. 13a, with approximate alignment of the ion inlet 1304, the inter-analyzer aperture 1312 and the ion outlet 1318. FIG. 13b is taken by cutting through the FAIMS 1300 in a plane that passes through the aligned ion inlet 1304, the inter-analyzer opening 1312 and the ion outlet 1318, and in practice the device extends longitudinally on both sides of this plane. Not-shown insulating material supports the electrodes in the spaced apart arrangement that is shown in FIG. 13b, and provides gas-tight seals that prevent gas from escaping around the peripheral parts of the electrodes. The not-shown insulating material ensures that gas flows into FAIMS 1300 only through the ion inlet 1304 and flows out of FAIMS 1300 only through the ion outlet 1318.

Still referring to FIGS. 13a and 13b, although there are curved regions between the electrodes, the alignment of the ion inlet 1304, the inter-analyzer opening 1312 and the ion outlet 1318 results in ions crossing the regions between the electrodes in a radial direction relative to the curvatures of the electrodes. This differs from a conventional mode of operation of ion separation in FAIMS where the ions are carried along the space between the electrodes in a direction generally parallel to the surfaces of the electrodes. FIGS. 13a and 13b illustrate the FAIMS device 1300 operating in a non-separating, total ion transmission mode. The distance between the ion inlet 1304 and the ion outlet 1318 is minimized.

FIGS. 14a and 14b illustrate the FAIMS 1300 of FIG. 13a, but with the intermediate electrode 1310 translated along the longitudinal direction so that the position of the inter-analyzer opening 1312 is displaced a distance "A" from the line-of-sight pathway between the ion inlet 1304 and the ion outlet 1318. FIG. 14b also illustrates an average ion flow path followed by a stream of ions 1402 and passing through ion inlet 1304, along a path approximately parallel to the surfaces of the electrodes to the inter-analyzer opening 1312, passing through the inter-analyzer opening 1312 and again following a path approximately parallel to the surfaces of the electrodes to the ion outlet 1318. The stream of ions 1404 that has passed through the ion outlet 1318 is then provided to a further not-shown post-FAIMS device that is optionally one of a mass spectrometer, an ion detector, a drift type ion mobility spectrometer, or to another FAIMS, as some non-limiting examples.

Still referring to FIGS. 14a and 14b, it is beneficial that the intermediate electrode 1310 is translatable for modifying the length of the path that the ions take when passing from the ion inlet 1304 to the ion outlet 1318. The displacement of the inter-analyzer opening 1312 in FIGS. 14a and 14b results in a pathway approximately twice the displacement "A". In normal ion separation mode with the asymmetric waveform and dc compensating offset voltages applied to the intermediate electrode 1310, the FAIMS separation takes place as the ions are carried along this pathway from the ion inlet 1304 to the inter-analyzer opening 1312, and from the inter-analyzer opening 1312 to the ion outlet 1318. The electric fields vary in strength in the radial direction from each of the curved electrodes 1306 and 1314 towards the intermediate electrode 1310. This variation in electric field strength, E/N, and the applied asymmetric waveform establishes the ion focusing mechanism that is beneficially used to minimize the loss of ions of interest, which are transmitted through FAIMS 1300 at the appropriate DV and CV, to the electrode surfaces.

Still referring to FIGS. 14a and 14b, the time required for transit through this device is beneficially controlled by the relative offset distance "A" that the ions travel to pass through the intermediate electrode. A longer distance "A" improves ion separation, but also increases the period of time required for ions to travel through the FAIMS device. Similarly, the effective separation may be reduced for a beneficial change in the time response of the device when the distance "A" in FIGS. 14a and 14b is minimized. FIGS. 13a and 13b illustrate the condition at the extreme of "A" being nearly zero such that the separation is not effective and the device operates in total ion transmission mode, where specificity is low. In this non-separating mode that is illustrated in FIGS. 13a and 13b, the asymmetric waveform optionally is turned off, and dc voltages are applied to the three electrodes of FAIMS 1300 to maximize ion transmission efficiency between the ion inlet 1304 and the ion outlet 1318.

Figure 15A:
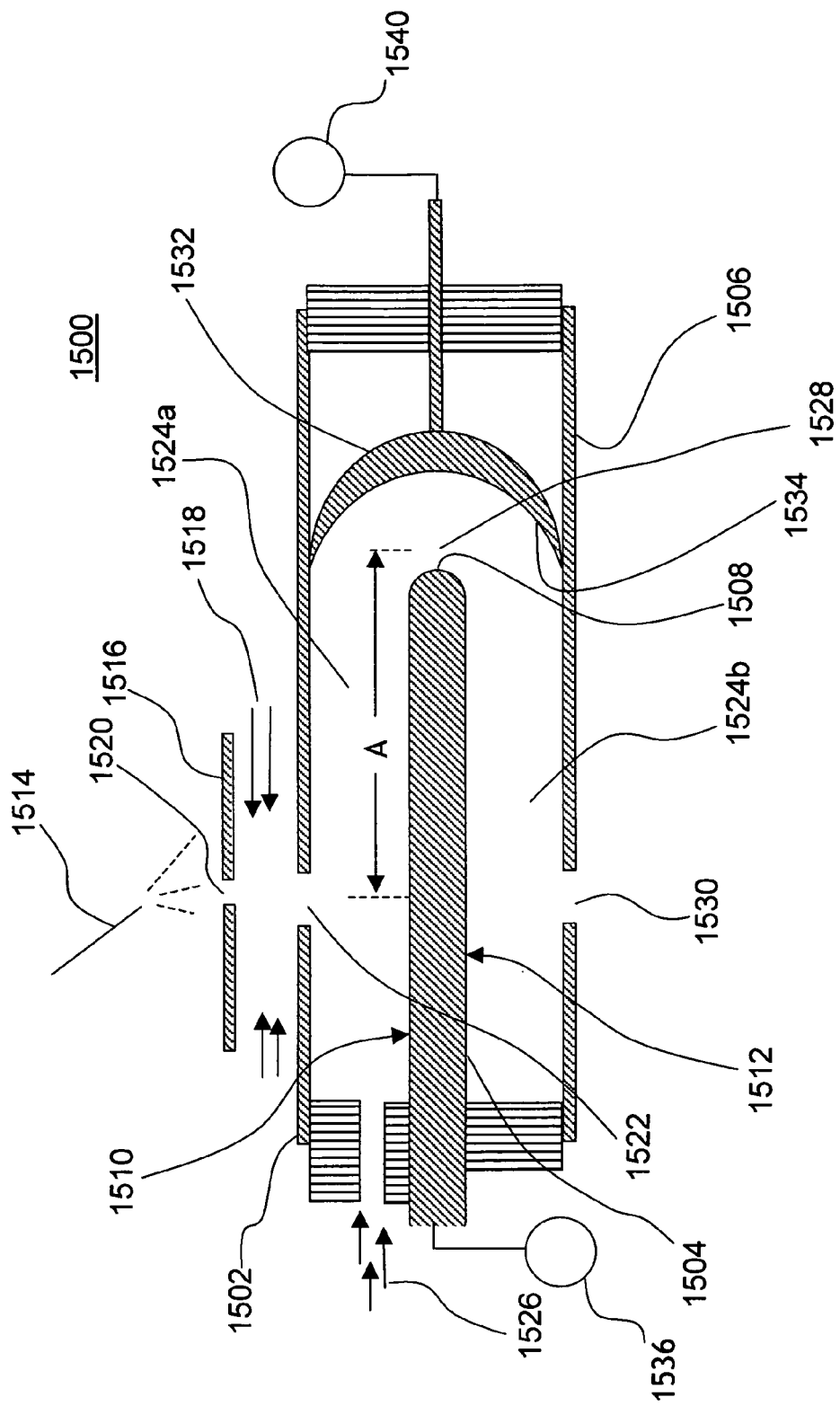
FIG. 15a is a longitudinal cross-sectional view of a parallel-plate geometry FAIMS, with a displacement A between an ion inlet and a transition point and between the transition point and an ion outlet.

Referring now to FIG. 15a, shown is a longitudinal cross-sectional view of a parallel plate FAIMS 1500 including three stacked plates 1502, 1504 and 1506, disposed in a spaced-apart relationship. The central electrode 1504 includes a curved terminus 1508 that is continuous with a first electrode surface 1510 on one side of the electrode 1504 and with a second electrode surface 1512 on a second side of the electrode 1504 that is opposite the first side. Ions that are produced by ion source 1514 drift toward a curtain plate 1516. A flow of a curtain gas 1518, introduced below the curtain plate 1516, divides into two portions, one of which flows outwardly through an aperture 1520 in the curtain plate 1516 so as to prevent neutrals and droplets from entering the curtain plate aperture 1520. Ions are driven against this flow of gas by a voltage gradient that is established between the ion source 1514 and the curtain plate 1516. A field generated by a voltage difference between the curtain plate 1516 and the FAIMS plate 1502 pushes ions that pass through the aperture 1520 in the curtain plate 1516 towards the ion inlet 1522 of FAIMS 1500. The second portion of the curtain gas flows into the ion inlet 1522 and carries the ions along the length of the FAIMS electrodes through the analyzer region 1524a. A second carrier gas flow 1526 is optionally provided to assist in carrying the ions along the analyzer region 1524a. The ions travel an approximate distance indicated as "A" from the inlet 1522 to a transition point 1528, defined near the end of the terminus 1508. The ions are carried by the flow of gas past the transition point 1528 and around the curved terminus 1508 into a second analyzer region 1524b, and travel a second distance "A" to the ion outlet 1530. Since the asymmetric waveform and dc offset voltage is applied to the plate 1504 from power supply 1536, and assuming that the distance between plate 1502 and 1504 and the distance between plate 1504 and 1506 are approximately equal, both analyzer regions 1524a and 1524b operate to separate ions in a substantially equivalent way. Optionally, to improve ion separation resolution, slightly different conditions are imposed in these analyzer regions 1524a and 1524b, by varying electrode spacing, by application of different dc voltages to plates 1502 and 1506 or by the application of different temperatures to the plates 1502 and 1506.

Referring still to FIG. 15a, a curved electrode 1532 is disposed between the plates 1502 and 1506. The curved electrode 1532 includes a concave electrode surface 1534 facing the curved terminus 1508. The concave electrode surface 1534 maintains an approximately constant spacing to the plate 1504 between the analyzer region 1524a and the analyzer region 1524b. Optionally, the curved electrode 1532 is electrically isolated from the electrode plates 1502 and 1506. For instance, not illustrated electrically insulating material is disposed between the ends of the curved electrode 1532 and the plates 1502 and 1506. Of course, the electrically insulating material forms a gas-tight seal to the plates 1502 and 1506 whilst supporting sliding motion of the curved electrode 1532. In that case, a dc voltage applied by optional power supply 1534 is independent of applied dc voltages to plates 1502 and 1506. By selection of appropriate applied dc voltages to each of the plates, optimized conditions for transmitting ions past the transition point 1528 are provided. Alternatively, the curved electrode 1532 is in electrical contact with plates 1502 and 1506.

Figure 15B:
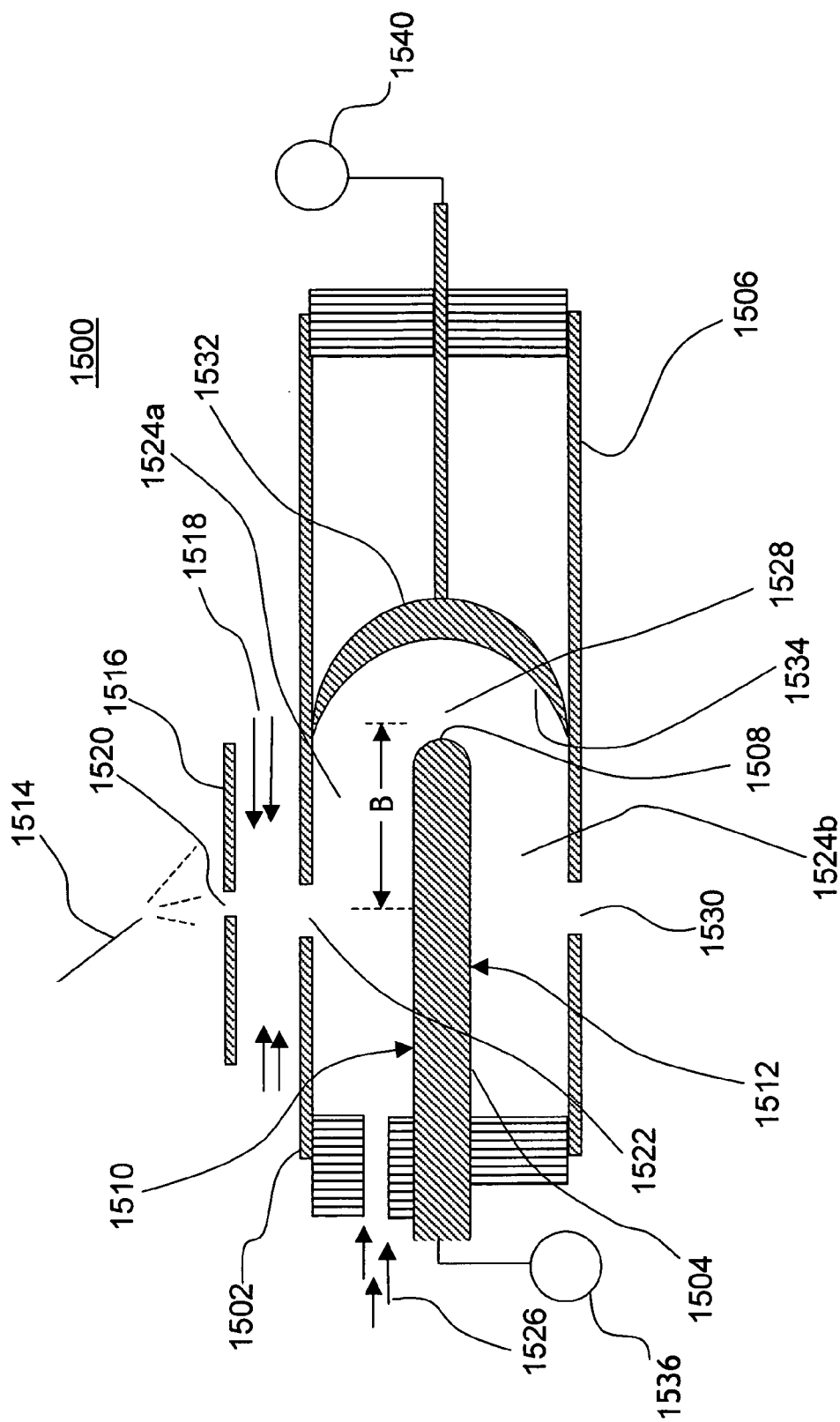
FIG. 15b is a longitudinal cross-sectional view of the parallel-plate geometry FAIMS of FIG. 15a, with a displacement B between the ion inlet and the transition point and between the transition point and the ion outlet.

Referring now to FIG. 15b, shown is a longitudinal cross-sectional view of the FAIMS 1500 of FIG. 15a, with the central electrode 1504 and curved electrode 1532 translated relative to plates 1502 and 1506, such that the position of the transition point 1528 is displaced a distance "B" from the ion inlet 1522 and the ion outlet 1530. In particular, the central plate 1504 and curved electrode 1532 are translated by equal amounts along a same direction, such that the spacing between the curved terminus 1508 and the concave surface 1534 is unchanged from the spacing shown in FIG. 15a. Ions traveling along an average ion flow path between the ion inlet 1522 and the ion outlet 1530 traverse a distance of approximately twice the distance "B" plus the thickness of plate 1504. Accordingly, given substantially identical operating conditions, ions spend less time being separated when the system 1500 is in the state shown in FIG. 15b compared to the state shown in FIG. 15a, in which ions traverse a greater distance of approximately twice the distance "A" plus the thickness of plate 1504. Thus, ions having similar FAIMS separation properties may be separated when the system 1500 is in the state shown in FIG. 15a, but may not be separated when the system 1500 is in the state shown in FIG. 15b. As such, varying the distance between the transition point 1528 and ion inlet 1522 and ion outlet 1530 supports controllably varying specificity of a FAIMS-based ion separation.

Figure 15C:
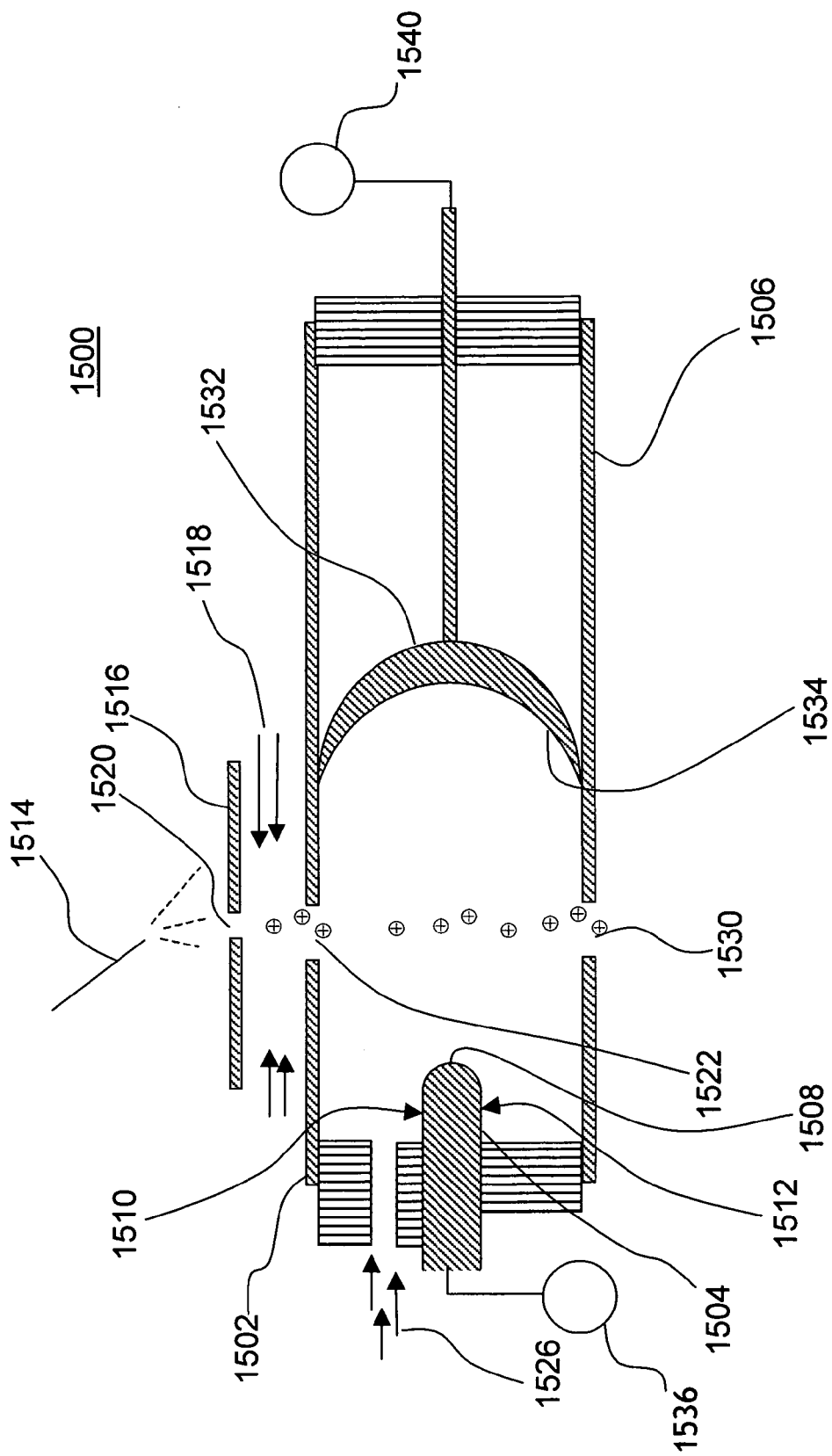
FIG. 15c is a longitudinal cross-sectional view of the parallel-plate geometry FAIMS of FIG. 15a, in a total ion transmission operating mode.

Referring now to FIG. 15c, shown is a longitudinal cross-sectional view of the FAIMS 1500 of FIG. 15a, with the plate 1504 and curved electrode 1532 translated away from each other, such that the plate 1504 is no longer disposed in the line-of-sight pathway between the ion inlet 1522 and the ion outlet 1530. In the state of system 1500 shown in FIG. 15c, ions pass along a shortest ion pathway between the ion inlet 1522 and the ion outlet 1530. Optionally, the asymmetric waveform applied to plate 1504 is shut off. Further optionally, an electric field gradient is established between plate 1502 and plate 1506 for driving ions from the ion inlet 1522 to the ion outlet 1530.

Referring still to FIG. 15c, a not illustrated actuator for translating the plate 1504 independently of the curved electrode 1532 is provided. Optionally, the actuator also supports synchronized translation of the plate 1504 and of the curved electrode 1532, so as to vary the distance between transition point 1528 and the ion inlet 1522 and the ion outlet 1530, as shown in FIGS. 15*a* and 15*b*, whilst maintaining approximately the same spacing from the curved terminus 1508 to the concave surface 1534.

Figure 16:
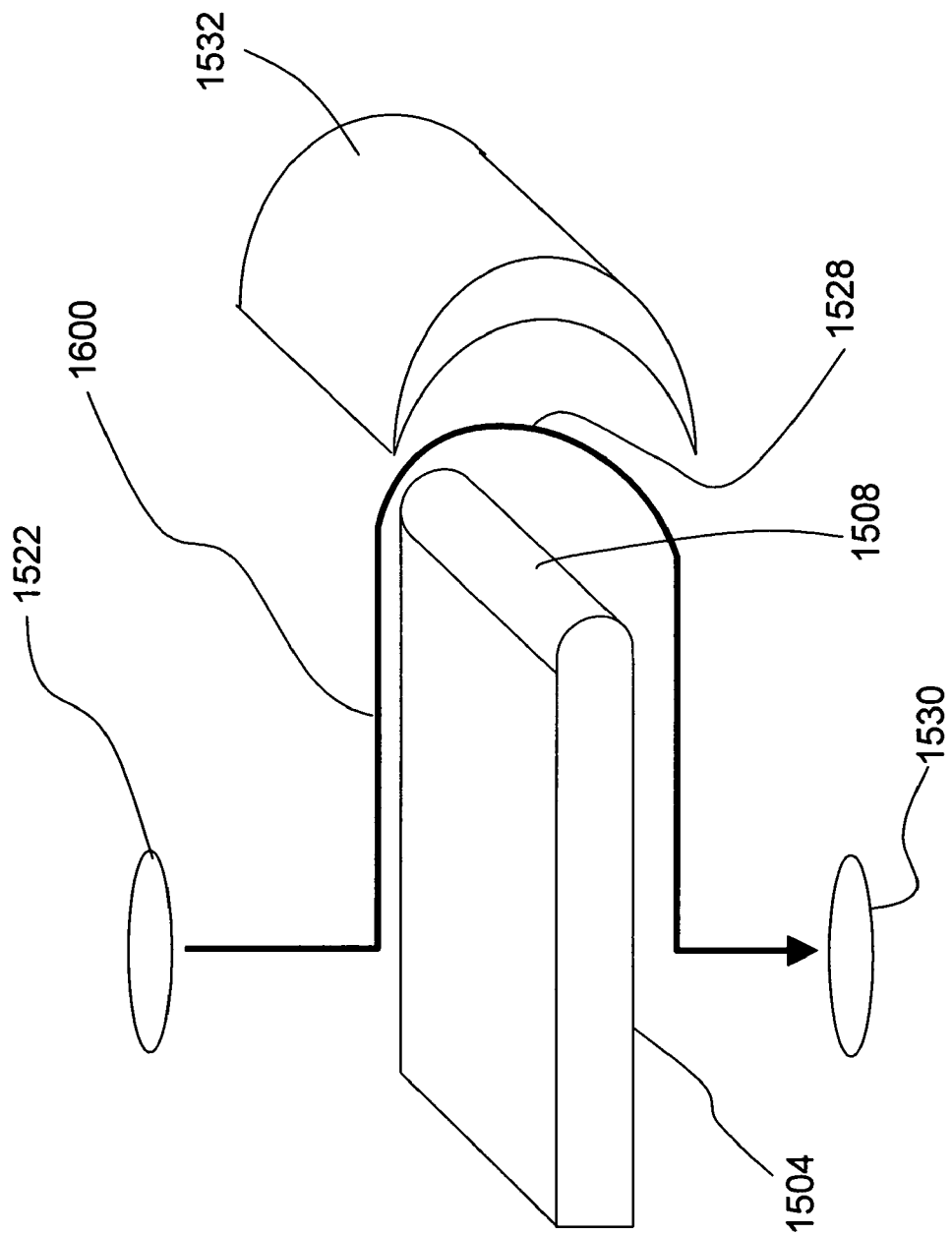
FIG. 16 is a perspective view of the middle plate of the FAIMS system of FIG. 15a disposed in a spaced apart relationship relative to the curved electrode of the FAIMS system of FIG. 15a, and showing an average ion flow path; and, FIG. 17 is a simplified flow diagram of a method for controllably varying specificity of a FAIMS-based ion separation according to an embodiment of the instant invention.

Referring now to FIG. 16, shown is a perspective view of the plate 1504 disposed in a spaced apart relationship relative to the curved electrode 1532. An average ion flow path 1600 is shown between the ion inlet 1522 and the ion outlet 1530, and passing through the transition point 1528.

Optionally, a form of side-to-side FAIMS is obtained by modification of the device shown at FIGS. 15*a*–15*c*. For instance, the plate 1504 is modified such that a second curved terminus is provided at an end of the plate 1504 opposite the curved terminus 1508. A second concave surface is disposed adjacent the second curved terminus, and the plate 1504 arranged approximately symmetrically with respect to a line passing through the ion inlet 1522 and the ion outlet 1530. In this not illustrated alternative embodiment, a second average ion flow path is defined between the ion inlet 1522 and the ion outlet 1530 that passes through a second transition point adjacent to the second curved terminus. Optionally, during use the modified plate is translated along one direction or the other, parallel to the plates 1502 and 1506. In this way, one of the average ion flow paths is lengthened, whilst the second average ion flow path is shortened. Alternatively, the modified plate is expandable, such that each of the two average ion flow paths is independently variable. Of course, a system including an expandable electrode plate is complicated, and provisions must be made to support the electrode plate and to ensure proper gas flow directionality.

Figure 17:
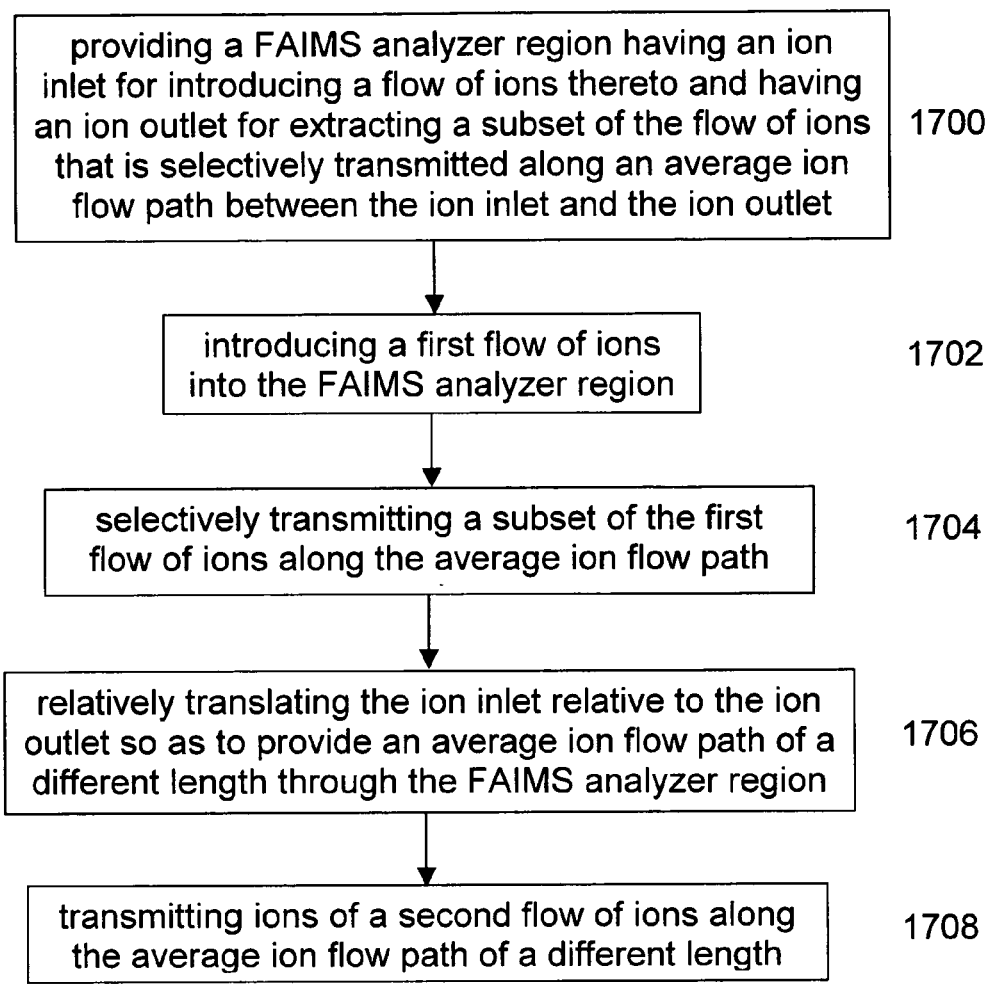

Referring now to FIG. 17, shown is a simplified flow diagram of a method for controllably varying specificity of a FAIMS-based ion separation according to an embodiment of the instant invention. At step 1700 a FAIMS analyzer region is provided, the FAIMS analyzer region having an ion inlet for introducing a flow of ions thereto and having an ion outlet for extracting a subset of the flow of ions that is selectively transmitted along an average ion flow path between the ion inlet and the ion outlet. At step 1702 a first flow of ions is introduced into the FAIMS analyzer region via the ion inlet. At step 1704 a subset of the first flow of ions is selectively transmitted along the average ion flow path through the FAIMS analyzer region. At step 1706 the ion inlet is relatively translated relative to the ion outlet so as to provide an average ion flow path of a different length through the FAIMS analyzer region. At step 1708 ions of a second flow of ions are transmitted along the average ion flow path of a different length.

In one particular use, which is given by way of a non-limiting example, an ion composition of the first flow of ions is substantially the same as an ion composition of the second flow of ions. For instance, the first and second flows of ions are produced at a same ionization source from a same sample material. Then, when having translated the ion inlet relative to the ion outlet to operate in the non-FAIMS separating TITM mode the ions of the second flow of ions that are transmitted along the second average ion flow path length has an ion composition substantially the same as the ion composition of the second flow of ions. In this case, the average ion flow path is equal to a straight-line distance or shortest path between the ion inlet and the ion outlet. Under this condition, the length of the FAIMS analyzer region is considered to be approximately zero. Optionally, appropriate conditions such as for example an electric field gradient between the ion inlet and the ion outlet or an appropriate gas flow are provided for directing the ions of the second flow between the ion inlet and the ion outlet.

Numerous other embodiments may be envisaged without departing from the spirit and scope of the invention.

What is claimed is:

1. An apparatus for controllably varying specificity of a FAIMS-based ion separation, comprising:
    a first electrode comprising a first electrode surface;
    a second electrode comprising a second electrode surface, the second electrode spaced-apart from the first electrode along a first direction such that the second electrode surface faces the first electrode surface and overlaps therewith along a second direction that is normal to the first direction so as to define a FAIMS analyzer region therebetween, the FAIMS analyzer region having an ion inlet end and an ion outlet end, the first electrode and the second electrode movable one relative to the other along the second direction for varying a length of the FAIMS analyzer region between the ion inlet end and the ion outlet end; and,
    an actuator for controllably relatively moving the first electrode along the second direction relative to the second electrode, for varying the length of the FAIMS analyzer region between the ion inlet end and the ion outlet end.

2. An apparatus according to claim 1, wherein the actuator is for supporting controllable movement of the first electrode relative to the second electrode to a position in which the length of the FAIMS analyzer region is approximately zero.

3. An apparatus according to claim 1, wherein the actuator comprises a motor coupled to one of the first electrode and the second electrode via a linkage member.

4. An apparatus according to claim 1, wherein the actuator comprises a manually operable mechanism coupled to one of the first electrode and the second electrode.

5. An apparatus according to claim 1, wherein the first electrode and the second electrode comprise inner and outer generally cylindrical electrodes, respectively, disposed in a concentric arrangement relative to a longitudinal axis defined along the second direction.

6. An apparatus according to claim 5, comprising a second inner electrode longitudinally spaced apart from the first electrode and coaxial therewith, a gap between the first electrode and the second inner electrode defining an ion inlet adjacent the ion inlet end, and further comprising an ion outlet defined within a portion of the second electrode and adjacent the ion outlet end.

7. An apparatus according to claim 6, comprising an ionization source in fluid communication with the ion inlet end via the ion inlet.

8. An apparatus according to claim 7, wherein the actuator is for translating the first electrode relative to the second electrode.

9. An apparatus according to claim 8, wherein the actuator is for translating the second inner electrode synchronously with the first electrode, such that the gap between the first electrode and the second inner electrode is approximately constant during translation.

10. An apparatus according to claim 7, wherein the actuator is for translating the second electrode relative to the first electrode.

11. An apparatus for controllably varying specificity of a FAIMS-based ion separation, comprising:
    a first generally cylindrical inner electrode having a first length;
    a second generally cylindrical inner electrode having a second length, the second generally cylindrical inner electrode axially aligned with and longitudinally spaced-apart from the first generally cylindrical inner electrode so as to define a circumferential gap between facing ends thereof, the circumferential gap defining an ion inlet;

an outer generally cylindrical electrode having a third length and disposed in a concentric overlapping arrangement with the first generally cylindrical inner electrode and with the second generally cylindrical inner electrode, the outer generally cylindrical electrode defining an ion outlet within a portion thereof, a space between the second generally cylindrical inner electrode and the outer generally cylindrical electrode defining a FAIMS analyzer region, an average ion flow path being defined through said FAIMS analyzer region between the ion inlet and the ion outlet; and, an actuator for relatively translating the outer generally cylindrical electrode relative to both the first generally cylindrical inner electrode and the second generally cylindrical inner electrode, so as to vary a length of the average ion flow path between the ion inlet and the ion outlet.

12. An apparatus according to claim 11, comprising an ionization source in fluid communication with the FAIMS analyzer region via the ion inlet.

13. An apparatus according to claim 12, wherein the ionization source is at least partially contained within the first generally cylindrical inner electrode.

14. An apparatus according to claim 11, comprising an electrical controller operatively coupled to the second generally cylindrical inner electrode for establishing an electric field between the second generally cylindrical inner electrode and the outer generally cylindrical electrode by application of an asymmetric waveform voltage and a direct current compensation voltage.

15. An apparatus according to claim 11, comprising a temperature controller for controllably establishing a temperature gradient within a gas flow between the second generally cylindrical inner electrode and the outer generally cylindrical electrode.

16. An apparatus according to claim 11, comprising a temperature controller for controllably adjusting a temperature of at least one of the second generally cylindrical inner electrode and the outer generally cylindrical electrode.

17. An apparatus according to claim 11, wherein the actuator is for translating the second generally cylindrical inner electrode synchronously with the first generally cylindrical inner electrode, such that the gap between the first generally cylindrical inner electrode and the second generally cylindrical inner electrode is approximately constant during translation.

18. A method for controllably varying specificity of a FAIMS-based ion separation, comprising:

providing a FAIMS analyzer region having an ion inlet for introducing a flow of ions thereto and having an ion outlet for extracting a subset of the flow of ions that is selectively transmitted along an average ion flow path between the ion inlet and the ion outlet;

introducing a first flow of ions into the FAIMS analyzer region via the ion inlet;

selectively transmitting a subset of the first flow of ions along the average ion flow path through the FAIMS analyzer region;

relatively translating the ion inlet relative to the ion outlet so as to provide an average ion flow path of a different length through the FAIMS analyzer region; and, transmitting ions of a second flow of ions along the average ion flow path of a different length.

19. A method according to claim 18, wherein an ion composition of the first flow of ions is substantially the same as an ion composition of the second flow of ions.

20. A method according to claim 19, wherein transmitting ions of the second flow of ions comprises selectively transmitting a subset of the second flow of ions, an ion composition of the subset of the second flow of ions being different than an ion composition of the subset of the first flow of ions.

21. A method according to claim 19, wherein transmitting ions of the second flow of ions comprises transmitting a set of ions having an ion composition substantially the same as the ion composition of the second flow of ions.

22. A method according to claim 18, wherein the FAIMS analyzer region is defined by a space between a first electrode surface and a second electrode surface, the first electrode surface disposed in a facing arrangement relative to the second electrode surface and spaced apart therefrom along a first direction, the first electrode surface defining the ion inlet and the second electrode surface defining the ion outlet, and wherein changing the length of the average ion flow path comprises relatively translating the first electrode surface relative to the second electrode surface along a second direction normal to the first direction.

23. An apparatus for controllably varying specificity of a FAIMS-based ion separation, comprising:

a FAIMS analyzer region defined between a first electrode surface and a second other electrode surface, the FAIMS analyzer region in communication with an ionization source for providing a flow of ions including a known ion, and with an ion outlet for extracting ions including the known ion from the FAIMS analyzer region, the first and second electrode surfaces for having an asymmetric waveform voltage applied thereacross for defining an average ion flow path for the known ion traversing therebetween; and, an actuator for controllably moving the first electrode surface relative to the second electrode surface for controllably varying the length of the average ion flow path.

24. An apparatus for controllably varying specificity of a FAIMS-based ion separation, comprising:

a FAIMS analyzer region controllably switchable between a low specificity mode of operation and a high specificity mode of operation and defined by at least a space between a plurality of spaced-apart electrode surfaces, the FAIMS analyzer region in communication with an ionization source for providing a flow of ions including a known ion, and with an ion outlet for extracting ions including the known ion from the FAIMS analyzer region, wherein switching between the low specificity mode of operation and the high specificity mode of operation is accomplished by repositioning at least one electrode surface of the plurality of spaced-apart electrode surfaces relative to another electrode surface of the plurality of spaced-apart electrode surfaces.

* * * * *